(12) United States Patent
Kim et al.

(10) Patent No.: US 11,649,436 B2
(45) Date of Patent: May 16, 2023

(54) EXOSOME FOR STIMULATING T CELL AND PHARMACEUTICAL USE THEREOF

(71) Applicant: THE CATHOLIC UNIVERSITY OF KOREA INDUSTRY—ACADEMIC COOPERATION FOUNDATION, Seoul (KR)

(72) Inventors: Tai Gyu Kim, Seoul (KR); Hyun Jung Sohn, Seoul (KR); Su Eon Kim, Yongin-si (KR)

(73) Assignee: THE CATHOLIC UNIVERSITY OF KOREA INDUSTRY-ACADEMIC COOPERATION FOUNDATION, Seoul (KR)

(*) Notice: Subject to any disclaimer, the term of this patent is extended or adjusted under 35 U.S.C. 154(b) by 858 days.

(21) Appl. No.: 16/465,919

(22) PCT Filed: Dec. 1, 2017

(86) PCT No.: PCT/KR2017/013981
§ 371 (c)(1),
(2) Date: May 31, 2019

(87) PCT Pub. No.: WO2018/101782
PCT Pub. Date: Jun. 7, 2018

(65) Prior Publication Data
US 2020/0071668 A1    Mar. 5, 2020

(30) Foreign Application Priority Data
Dec. 2, 2016  (KR) .................. 10-2016-0163822

(51) Int. Cl.
| | | |
|---|---|---|
| *A61K 8/14* | (2006.01) | |
| *A61K 9/127* | (2006.01) | |
| *C07K 14/705* | (2006.01) | |
| *C07K 14/715* | (2006.01) | |
| *C12N 5/0783* | (2010.01) | |
| *C07K 14/735* | (2006.01) | |
| *C07K 14/74* | (2006.01) | |

(52) U.S. Cl.
CPC ...... *C12N 5/0636* (2013.01); *C07K 14/70532* (2013.01); *C07K 14/70535* (2013.01); *C07K 14/70539* (2013.01); *C07K 14/70596* (2013.01); *C07K 14/7151* (2013.01); *C12N 5/0638* (2013.01); *C12N 2501/25* (2013.01); *C12N 2501/51* (2013.01); *C12N 2501/599* (2013.01)

(58) Field of Classification Search
CPC ........ A61K 9/127; A61K 8/14; A61K 49/008; C12N 5/0636; C07K 14/70596; C07K 14/70539; C07K 14/70532; C07K 14/70535; C07K 14/7151
See application file for complete search history.

(56) References Cited

U.S. PATENT DOCUMENTS

| | | | |
|---|---|---|---|
| 2006/0034810 A1* | 2/2006 | Riley ..................... | A61P 37/04 424/93.21 |
| 2010/0092524 A1* | 4/2010 | Taylor ................ | A61K 39/0011 424/277.1 |
| 2016/0038576 A1* | 2/2016 | Vasserot ................ | C07K 16/28 435/69.3 |

FOREIGN PATENT DOCUMENTS

| | | |
|---|---|---|
| CN | 103966165 A | 8/2014 |
| WO | 2013102219 A1 | 7/2013 |

OTHER PUBLICATIONS

Kalluri et al. The biology, function, and biomedical applications of exosomes. Science 367(6478): eaau6977, 2020.*
Leone et al. Dendritic cells and routing cargo into exosomes. Immunol Cell Biol 96: 683-693, 2018.*
Cho et al. Triple costimulation via CD80, 4-1BB, and CD83 ligand elicits the long-term growth of Vgamma9Vdelta2 T cells in low levels of IL-2. J Leukoc Biol 99: 521-529, 2016.*
International Search Report issued by the International Searching Authority (KR) in PCT Application No. PCT/KR2017/013981 dated Mar. 26, 2018. 5 pages.
GenBank DQ892356.2. "Synthetic construct clone IMAGE:100004986; FLH185494.01X; RZPDo839B10148D CD83 molecule (CD83) gene, encodes complete protein." Mar. 21, 2007, 3 pages.
GenBank U02935.2. "*Homo sapiens* HLA-A2 gene, enhancer region and complete cds." Jul. 25, 2003, 3 pages.
GenBank U03398.1. "Human receptor 4-1BB ligand mRNA, complete cds." Nov. 27, 1994, 2 pages.
Kim, Sueon, et al. "Engineered Exosomes Expressing HLA and Co-Stimulatory Molecules to Generate Antigen-Specific CD8+ T Cells for Adoptive Cell Therapy." (2016): 1338-1338.
Kim, Sueon, et al. "Use of engineered exosomes expressing HLA and costimulatory molecules to generate antigen-specific CD8+ T cells for adoptive cell therapy." Journal of Immunotherapy 40.3 (2017): 83-93.
NCBI Reference Sequence NM_005191.3. "*Homo sapiens* CD80 molecule (CD80), mRNA." Oct. 6, 2016, 5 pages.
Suhoski, Megan M., et al. "Engineering artificial antigen-presenting cells to express a diverse array of co-stimulatory molecules." Molecular Therapy 15.5 (2007): 981-988.
Turtle, Cameron J., and Stanley R. Riddell. "Artificial antigen presenting cells for use in adoptive immunotherapy." Cancer Journal. 16.4 (2010): 374-381.

* cited by examiner

*Primary Examiner* — Bridget E Bunner
(74) *Attorney, Agent, or Firm* — Meunier Carlin & Curfman LLC

(57) ABSTRACT

The present invention relates to an exosome for stimulating T cells and the pharmaceutical use thereof. Immune exosomes secreted from artificial antigen-presenting cells which express HLA, CD32, and co-stimulatory molecules CD32, CD80, CD83, and 4-1BBL are used to stimulate naive CD8+ T cells whereby preventive and therapeutic effects on tumors, pathogen infections, or autoimmune diseases can be provided.

4 Claims, 14 Drawing Sheets

Specification includes a Sequence Listing.

a b

SEQUENCE LISTING

```
<160> NUMBER OF SEQ ID NOS: 16

<210> SEQ ID NO 1
<211> LENGTH: 1104
<212> TYPE: DNA
<213> ORGANISM: Homo sapiens

<400> SEQUENCE: 1
atggccgtca tggcgccccg aaccctcgtc ctgctactct cggggggctct ggccctgacc      60 cagacctggg cgggctctca ctccatgagg tatttcttca catccgtgtc ccggcccggc     120
cgcggggagc cccgcttcat cgcagtgggc tacgtggacg acacgcagtt cgtgcggttc     180
gacagcgacg ccgcgagcca gaggatggag ccgcgggcgc cgtggataga gcaggagggt     240
ccggagtatt gggacgggga gacacggaaa gtgaaggccc actcacagac tcaccgagtg     300
gacctgggga ccctgcgcgg ctactacaac cagagcgagg ccggttctca caccgtccag     360
aggatgtatg gctgcgacgt ggggtcggac tggcgcttcc tccgcgggta ccaccagtac     420
gcctacgacg gcaaggatta tatcgccctg aaagaggacc tgcgctcttg gaccgcggcg     480
gacatggcag ctcagaccac caagcacaag tgggaggcgg cccatgtggc ggagcagttg     540
agagcctacc tggagggcac gtgcgtggag tggctccgca gatacctgga gaacgggaag     600
gagacgctgc agcgcacgga cgcccccaaa acgcatatga ctcaccacgc tgtctctgac     660
catgaagcca ccctgaggtg ctgggccctg agcttctacc ctgcggagat cacactgacc     720
tggcagcggg atggggagga ccagacccag gacacggagc tcgtggagac caggcctgca     780 ggggatgaa ccttccagaa gtgggcggct gtggtggtgc cttctggaca ggagcagaga     840
tacacctgcc atgtgcagca tgagggtttg cccaagcccc tcaccctgag atgggagccg     900
tcttcccagc ccaccatccc catcgtgggc atcattgctg gcctggttct ctttggagct     960
gtgatcactg gagctgtggt cgctgctgtg atgtggagga ggaagagctc agatagaaaa    1020
ggagggagct actctcaggc tgcaagcagt gacagtgccc agggctctga tgtgtctctc    1080
acagcttgta aagtgtgaat gatt                                           1104
```

<210> SEQ ID NO 2
<211> LENGTH: 1734
<212> TYPE: DNA
<213> ORGANISM: Homo sapiens

<400> SEQUENCE: 2

| | | | | | |
|---|---|---|---|---|---|
| atgggccaca | cacggaggca | gggaacatca | ccatccaagt | gtccatacct | caatttcttt | 60 |
| cagctcttgg | tgctggctgg | tctttctcac | ttctgttcag | gtgttatcca | cgtgaccaag | 120 |
| gaagtgaaag | aagtggcaac | gctgtcctgt | ggtcacaatg | tttctgttga | agagctggca | 180 |
| caaactcgca | tctactggca | aaaggagaag | aaaatggtgc | tgactatgat | gtctggggac | 240 |
| atgaatatat | ggcccgagta | caagaaccgg | accatctttg | atatcactaa | taacctctcc | 300 |
| attgtgatcc | tggctctgcg | cccatctgac | gagggcacat | acgagtgtgt | tgttctgaag | 360 |
| tatgaaaaag | acgctttcaa | gcgggaacac | ctggctgaag | tgacgttatc | agtcaaagct | 420 |
| gacttcccta | cacctagtat | atctgacttt | gaaattccaa | cttctaatat | tagaaggata | 480 |
| atttgctcaa | cctctggagg | ttttccagag | cctcacctct | cctggttgga | aaatggagaa | 540 |
| gaattaaatg | ccatcaacac | aacagtttcc | caagatcctg | aaactgagct | ctatgctgtt | 600 |
| agcagcaaac | tggatttcaa | tatgacaacc | aaccacagct | tcatgtgtct | catcaagtat | 660 |
| ggacatttaa | gagtgaatca | gaccttcaac | tggaatacaa | ccaagcaaga | gcattttcct | 720 |
| gataacctgc | tcccatcctg | gccattacc | ttaatctcag | taaatggaat | ttttgtgata | 780 |
| tgctgcctga | cctactgctt | tgccccaaga | tgcagagaga | aaggaggaa | tgagagattg | 840 |
| agaagggaaa | gtgtacgccc | tgtataaatg | ggccacacac | ggaggcaggg | aacatcacca | 900 |
| tccaagtgtc | catacctcaa | tttctttcag | ctcttggtgc | tggctggtct | ttctcacttc | 960 |
| tgttcaggtg | ttatccacgt | gaccaaggaa | gtgaaagaag | tggcaacgct | gtcctgtggt | 1020 |
| cacaatgttt | ctgttgaaga | gctggcacaa | actcgcatct | actggcaaaa | ggagaagaaa | 1080 |
| atggtgctga | ctatgatgtc | tggggacatg | aatatatggc | ccgagtacaa | gaaccggacc | 1140 |
| atctttgata | tcactaataa | cctctccatt | gtgatcctgg | ctctgcgccc | atctgacgag | 1200 |
| ggcacatacg | agtgtgttgt | tctgaagtat | gaaaaagacg | ctttcaagcg | ggaacacctg | 1260 |
| gctgaagtga | cgttatcagt | caaagctgac | ttccctacac | ctagtatatc | tgactttgaa | 1320 |
| attccaactt | ctaatattag | aaggataatt | tgctcaacct | ctggaggttt | tccagagcct | 1380 |
| cacctctcct | ggttggaaaa | tggagaagaa | ttaaatgcca | tcaacacaac | agtttcccaa | 1440 |
| gatcctgaaa | ctgagctcta | tgctgttagc | agcaaactgg | atttcaatat | gacaaccaac | 1500 |
| cacagcttca | tgtgtctcat | caagtatgga | catttaagag | tgaatcagac | cttcaactgg | 1560 |
| aatacaacca | agcaagagca | ttttcctgat | aacctgctcc | catcctgggc | cattaccta | 1620 |
| atctcagtaa | atggaatttt | tgtgatatgc | tgcctgacct | actgctttgc | cccaagatgc | 1680 |
| agagagagaa | ggaggaatga | gagattgaga | agggaaagtg | tacgccctgt | ataa | 1734 |

<210> SEQ ID NO 3
<211> LENGTH: 618
<212> TYPE: DNA
<213> ORGANISM: Homo sapiens

<400> SEQUENCE: 3

| | | | | | |
|---|---|---|---|---|---|
| atgtcgcgcg | gcctccagct | tctgctcctg | agctgcgcct | acagcctggc | tcccgcgacg | 60 |
| ccggaggtga | aggtggcttg | ctccgaagat | gtggacttgc | cctgcaccgc | ccctggggat | 120 |
| ccgcaggttc | cctacacggt | ctcctgggtc | aagttattgg | agggtggtga | agagaggatg | 180 |

```
gagacacccc aggaagacca cctcagggga cagcactatc atcagaaggg gcaaaatggt    240
tctttcgacg cccccaatga aaggccctat tccctgaaga tccgaaacac taccagctgc    300
aactcgggga catacaggtg cactctgcag gacccggatg ggcagagaaa cctaagtggc    360
aaggtgatct tgagagtgac aggatgccct gcacagcgta aagaagagac ttttaagaaa    420
tacagagcgg agattgtcct gctgctggct ctggttattt tctacttaac actcatcatt    480
ttcacttgta agtttgcacg gctacagagt atcttcccag attttctaa agctggcatg     540 gaacgagctt ttctcccagt tacctcccca aataagcatt tagggctagt gactcctcac    600
aagacagaac tggtatag                                                  618

<210> SEQ ID NO 4
<211> LENGTH: 765
<212> TYPE: DNA
<213> ORGANISM: Homo sapiens

<400> SEQUENCE: 4
atggaatacg cctctgacgc ttcactggac cccgaagccc cgtggcctcc cgcgccccgc     60
gctcgcgcct gccgcgtact gccttgggcc ctggtcgcgg ggctgctgct gctgctgctg    120
ctcgctgccg cctgcgccgt cttcctcgcc tgcccctggg ccgtgtccgg ggctcgcgcc    180
tcgcccggct ccgcggccag cccgagactc cgcgagggtc ccgagctttc gcccgacgat    240
cccgccggcc tcttggacct gcggcagggc atgtttgcgc agctggtggc ccaaaatgtt    300
ctgctgatcg atgggcccct gagctggtac agtgacccag gctggcagg cgtgtccctg    360 acgggggggcc tgagctacaa agaggacacg aaggagctgg tggtggccaa ggctggagtc    420
tactatgtct tctttcaact agagctgcgg cgcgtggtgg ccggcgaggg ctcaggctcc    480
gtttcacttg cgctgcacct gcagccactg cgctctgctg ctggggccgc cgccctggct    540
ttgaccgtgg acctgccacc cgcctcctcc gaggctcgga actcggcctt cggtttccag    600
ggccgcttgc tgcacctgag tgccggccag cgcctgggcg tccatcttca cactgaggcc    660
agggcacgcc atgcctggca gcttacccag ggcgccacag tcttgggact cttccgggtg    720 accccgaaa tcccagccgg actcccttca ccgaggtcgg aataa                      765

<210> SEQ ID NO 5
<211> LENGTH: 9
<212> TYPE: PRT
<213> ORGANISM: Artificial Sequence
<220> FEATURE:
<223> OTHER INFORMATION: pp65 495-503

<400> SEQUENCE: 5

Asn Leu Val Pro Met Val Ala Thr Val
1               5

<210> SEQ ID NO 6
<211> LENGTH: 9
<212> TYPE: PRT
<213> ORGANISM: Artificial Sequence
<220> FEATURE:
<223> OTHER INFORMATION: LMP 1159-167

<400> SEQUENCE: 6

Tyr Leu Gln Gln Asn Trp Trp Thr Leu
1               5

<210> SEQ ID NO 7
```

```
<211> LENGTH: 10
<212> TYPE: PRT
<213> ORGANISM: Artificial Sequence
<220> FEATURE:
<223> OTHER INFORMATION: MART 126-35

<400> SEQUENCE: 7

Glu Leu Ala Gly Ile Gly Ile Leu Thr Val
1               5                   10

<210> SEQ ID NO 8
<211> LENGTH: 9
<212> TYPE: PRT
<213> ORGANISM: Artificial Sequence
<220> FEATURE:
<223> OTHER INFORMATION: WT 126-134

<400> SEQUENCE: 8

Arg Met Phe Pro Asn Ala Pro Tyr Leu
1               5

<210> SEQ ID NO 9
<211> LENGTH: 8
<212> TYPE: PRT
<213> ORGANISM: Artificial Sequence
<220> FEATURE:
<223> OTHER INFORMATION: Ova257

<400> SEQUENCE: 9

Ser Ile Ile Asn Phe Glu Lys Leu
1               5

<210> SEQ ID NO 10
<211> LENGTH: 9
<212> TYPE: PRT
<213> ORGANISM: Artificial Sequence
<220> FEATURE:
<223> OTHER INFORMATION: tyrosinase-related protein 1455 (Trp1455)

<400> SEQUENCE: 10

Thr Ala Pro Asp Asn Leu Gly Tyr Ala
1               5

<210> SEQ ID NO 11
<211> LENGTH: 9
<212> TYPE: PRT
<213> ORGANISM: Artificial Sequence
<220> FEATURE:
<223> OTHER INFORMATION: Trp2 180

<400> SEQUENCE: 11

Ser Val Tyr Asp Phe Phe Val Trp Leu
1               5

<210> SEQ ID NO 12
<211> LENGTH: 9
<212> TYPE: PRT
<213> ORGANISM: Artificial Sequence
<220> FEATURE:
<223> OTHER INFORMATION: gp100 25

<400> SEQUENCE: 12

Glu Gly Ser Arg Asn Gln Asp Trp Leu
1               5

<210> SEQ ID NO 13
<211> LENGTH: 9
```

```
<212> TYPE: PRT
<213> ORGANISM: Artificial Sequence
<220> FEATURE:
<223> OTHER INFORMATION: MAGE 1 nonapeptide

<400> SEQUENCE: 13

Glu Ala Asp Pro Thr Gly His Ser Tyr
1               5

<210> SEQ ID NO 14
<211> LENGTH: 9
<212> TYPE: PRT
<213> ORGANISM: Artificial Sequence
<220> FEATURE:
<223> OTHER INFORMATION: MART-APL peptide

<400> SEQUENCE: 14

Leu Ala Gly Ile Gly Ile Leu Thr Val
1               5

<210> SEQ ID NO 15
<211> LENGTH: 9
<212> TYPE: PRT
<213> ORGANISM: Artificial Sequence
<220> FEATURE:
<223> OTHER INFORMATION: natural peptide

<400> SEQUENCE: 15

Ala Ala Gly Ile Gly Ile Leu Thr Val
1               5

<210> SEQ ID NO 16
<211> LENGTH: 10
<212> TYPE: PRT
<213> ORGANISM: Artificial Sequence
<220> FEATURE:
<223> OTHER INFORMATION: PSA-1 peptide

<400> SEQUENCE: 16

Phe Leu Thr Pro Lys Lys Leu Gln Cys Val
1               5                   10
```

EXOSOME FOR STIMULATING T CELL AND PHARMACEUTICAL USE THEREOF

REFERENCE TO AN ELECTRONIC SEQUENCE LISTING

The content of the electronic sequence listing submitted on Aug. 5, 2022, as an TXT file named "10820_019US1_ST25.txt" created on Aug. 5, 2022, and having a size of 8,329 bytes, is hereby incorporated by reference in its entirety pursuant to 37 C.F.R. §§ 1.821-1.825.

BACKGROUND

1. Field of the Invention

The present invention relates to an exosome for stimulating T cells, which expresses HLA and co-stimulatory molecules, and the pharmaceutical use thereof.

2. Discussion of Related Art

Naive antigen-specific T cells may be directly stimulated by antigen-pulsed mature dendritic cells (DCs). Further, dendritic cells release antigen-presenting vesicles, so-called "exosomes" by processing antigens in endosomal compartments capable of binding to a cell membrane, e.g. multivesicular endosomes. A dendritic cell-derived exosome (DEX) is an effective stimulant of T cells. A more effective means of T cell activation by DEX appears to occur indirectly following DEX interactions with DCs. Two major mechanisms have been proposed to explain whether the antigen peptide-MHC-containing DEX may induce indirect antigen presentation in T cells by antigen presenting cells (APCs). First, by a process known as "cross-dressing", the DEX binds directly to the surface membrane of a receptor APC, transfers the peptide-MHC complex thereof to the APC membrane, and then is recognized by T cells without additional antigen processing. Second, the indirect presentation mechanism takes place by transferring the antigen to APC MHCs in the DEX MHC via the capture and re-processing of the DEX peptide-MHC complex by the APC. However, the generation of sufficient DEXs from the autologous DCs remains a barrier to the wide use of the DEX for immunotherapy.

The development of latex beads capable of being coupled to co-stimulatory molecules heralded a new area in artificial antigen-presenting cell (AAPC) technology. This approach enables precise control of signaling, but has some limitations. In particular, the interaction between T cells and beads is different from the interaction between T cells and natural APCs. The concept that a modified lipid surface may improve immune synapse formation is attractive, and preparations such as AAPCs began to be evaluated in recent studies. An advantage of cellular AAPCs is that once the cellular AAPCs are created, the cell line thereof may be approved and deposited, and thus is provided as a source of a preparation that may be easily accessed for a long period of time in order to be used for the production or expansion of T cells without any preparation of feeder cells, which is frequently required for methods of culturing autologous APCs or other T cells. In particular, mesenchymal stem cells, neural stem cells, embryonic stem cells, umbilical cord blood-derived cells, and chronic myelogenous leukemia K562 cell lines have been used for this purpose because they do not express endogenous HLA class I and II molecules.

The present invention facilitates a detailed analysis of contribution of these molecules to the proliferation of T cells by introducing various co-stimulatory molecules into K562 cells in order to additionally enhance signalling. For example, after CD8+ T cells are stimulated by K562 cells into which HLA-A2, CD32, CD80, and CD83 are introduced, CD8+ T cells specific for HLA-A2-restricted epitopes may be produced from MART1. In order to produce antigen-specific T cells for adoptive immunotherapy, several gene modified K562-based AAPCs have been used. K562 cells have been widely used as a high releasing model for an exosome which expresses a general exosome marker such as CD9, CD63, CD81, CD82, and Tsg101. Furthermore, an immunosome serving as a virus-like particle for non-specifically stimulating T cells in vitro from HEK293 cells by variation of T cell co-stimulatory ligands having a glycosylphosphatidylinositol (GPI) anchor that promotes the localization of a single-chain Fv (scFv) fragment of an OKT3 antibody and a lipid raft was developed.

The inventors established a hypothesis that K562 cells transduced with a vector which expresses not only CD32, CD80, CD83, and 4-1BBL, but also HLA-A2 would naturally release immunological exosomes comparable to DEX, and characterized the phenotype of an exosome derived from modified K562 cells, thereby completing the present invention.

SUMMARY OF THE INVENTION

An object of the present invention is directed to providing an exosome exhibiting an immunostimulatory reaction isolated from artificial antigen presenting cells which express HLA and co-stimulatory molecules, and the pharmaceutical use thereof.

To achieve the object, the present invention provides an exosome which expresses a human leukocyte antigen (HLA), CD32, CD80, CD83, and 4-1BBL.

The present invention also provides an immunotherapeutic agent including the exosome.

The present invention also provides a vaccine for preventing tumors, pathogen infections, or autoimmune diseases, including the exosome.

The present invention also provides a pharmaceutical composition for treating tumors, pathogen infections, or autoimmune diseases, including the exosome.

The present invention also provides a method for proliferating T cells, the method including a step of co-culturing the exosome and any one T cell of a CD4 T cell, a CD8 T cell, or a γδT cell.

The present invention also provides a method for preparing cytotoxic T cells in vitro, the method including a step of stimulating any one of a CD4 T cell, a CD8 T cell, or a γδT cell with the exosome sensitized with one or more antigens selected from the group consisting of a tumor antigen, a pathogen antigen, and an autoantibody.

The present invention uses immunological exosomes secreted from artificial antigen-presenting cells which express HLA and co-stimulatory molecules to stimulate naive CD8+ T cells whereby preventive and therapeutic effects on tumors, pathogen infections, or autoimmune diseases can be provided.

BRIEF DESCRIPTION OF THE DRAWINGS

FIG. 2 illustrates the efficient activation and proliferation of CD8+ T cells by using a K562-derived exosome (CoEX) which has no HLA-A2 and expresses CD32 and co-stimulatory molecules.

FIG. 4 illustrates the results of confirming immunostimulatory responses of a K562-derived exosome (CoEX-A2) which expresses HLA-A2 and co-stimulatory molecules.

FIG. 6a shows a comparison of activities of CMV antigen-specific CD8+ T cells treated with an exosome (CoEX-A2) which expresses $pp65_{495-503}$-loaded HLA-A2 and co-stimulatory molecules for the stimulation of CD8+ antigen-specific T cells from five HLA-A2+ and 2 HLA-A2-volunteers. FIG. 6b illustrates results in which CD8+ T cells are incubated with CoEX-A2 in the presence (+) or absence (−) of a $MART1_{26-35}$ peptide.

FIG. 7a is a view illustrating the uptake of K562 cell-derived exosomes modified by non-specific CD8+ T cells causing the stimulation of antigen-specific CD8+ T cell responses. CD8+ T cells treated with an exosome which expresses HLA-2 and a co-stimulatory molecule (CoEX-A2) obtained HLA-A2 and the co-stimulatory molecule of the exosome to cause the stimulation of an antigen-specific CD8+ T cell response by HLA-A2/TCR (Signal I), CD83, 41BBL, and CD80 co-stimulation (Signal II). FIG. 7b is a view illustrating that the uptake of 4 types of exosomes by K562 cells enables K562-mediated induction of antigen-specific CD8+T lymphocyte activation.

FIG. 9a illustrates FITC vs. SSC dot plot results for CFSE-labeled T2 cells (target cells). The graph exhibits the spontaneous apoptotic rate in a normal sample at an E:T ratio of 200:1 and represents CD8+ T cell activity. When T2 cells were cultured in the absence of a pp65 peptide, there was little apoptosis (less than 1.8%). When the ratio of antigen-specific CD8+ T cells:T2 cells was 200:1, the T cell apoptotic rate was increased up to >38%. FIG. 9b illustrates the degree of CTL toxicity according to the ratio of antigen-specific CD8+ T cells:T2 cells (that is, effector cell vs. target cell). T2 cells were labeled with CFSE and co-cultured with CTL at the ratio and at 37° C. for 6 hours. At the end of the experiment, dead cells were labeled with 7-AAD. The percentage of T cell apoptosis was measured by using flow cytometry. There was no significant difference in cell apoptosis between cells treated with CoEX-A2 and DEX.

DETAILED DESCRIPTION OF EXEMPLARY EMBODIMENTS

Figure 1A:
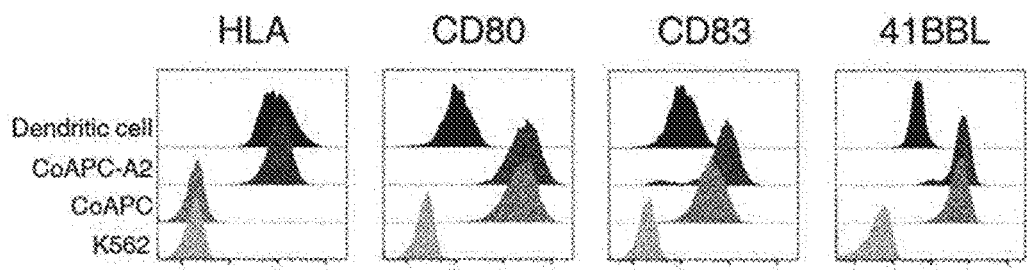
FIG. 1 illustrates a result of characterization of a K562-derived exosome (CoEX-A2) which expresses HLA-A2 and co-stimulatory molecules, and in FIG. 1a, K562 cells were transduced with a lentiviral vector carrying genes encoding HLA-A2, CD32, CD80, CD83, and CD137L(4-1BBL) and cultured without any antibiotic for 2 months by sorting the cells with a MoFlo cytometer to isolate single-cell clones, protein expression was detected by flow cytometry, and the histograms show protein expression levels in an A2-CD32-80-83-41BBL cell line (black) and a CD32-80-83-41BBL cell line (charcoal grey) as compared to K562 mother cells (bright grey).
FIG. 1b illustrates the results of culturing CD8+ T cells isolated from healthy volunteers together with an A2-CD32-80-83-41BBL (CoAPC-A2) cell line, a CD32-80-83-41BBL (CoAPC) cell line, and K562 cells and analyzing the cells in the presence (+) or absence (−) of a CMV peptide. Additionally, the cells were analyzed by using ModFit LT 3.0 software (Verity Software House). Representative staining from three independent experiments are shown. CD8+ T cells ($5 \times 10^5$) isolated from human peripheral blood mononuclear cells (PBMCs) were activated by using artificial antigen-presenting cells.
FIG. 1c illustrates flow cytometry analysis results of the expression of HLA-A2/co-stimulatory molecules of CoEX-A2 or the K562 cell-derived exosome (KEX).
FIG. 1d illustrates flow cytometry analysis results of exosomes coupled to latex beads coated with diverse exosome-specific marker antibodies, and for comparison, latex beads coated with an entire exosome preparation are included. The plot is a representation of the intensities derived from a control (grey) with the only corresponding bead and an exosome-specific antibody (black). Each plot is a representative value from three independent experiments.
FIG. 1e illustrates dot blot analysis results of CoEX-A2 lysates, the corresponding dot was evaluated by using an exosome antibody array kit, and the exosome-specific antibody spots provided signals at various degrees. The value is an average of three independent experiments performed in triplicate, and the error bar is SEM.

Hereinafter, the configuration of the present invention will be described in detail.

The present invention relates to exosomes which express a human leukocyte antigen (HLA), CD32, CD80, CD83, and 4-1BBL.

The present invention is characterized by providing exosomes as extracellular vesicles which are secreted from artificial antigen-presenting cells constructed so as to induce an antigen-specific cytotoxic T cell response and express HLA and co-stimulatory molecules CD32, CD80, CD83, and 4-BBL while performing the functions of autologous antigen-presenting cells as an alternative to solve the disadvantages in that conventional antigen-presenting cells, for example, dendritic cells are present in small amounts in human peripheral blood mononuclear cells and it is difficult to obtain a large amount of cells for clinical application.

As used herein, the term "artificial antigen-presenting cells (aAPCs)" refers to antigen-presenting cells artificially constructed, and the cells are non-immune cells modified so as to express immune molecules. The aAPC which expresses MHC Class I or II (MHC I or II) either alone or together with other accessory molecules (co-stimulatory molecules and/or adhesion molecules) is used to study various aspects of T cell activated cells which may be easily cultured in vivo, such as a cell line of tumor cells or fibroblasts. For the purpose of the present invention, the above term refers to cells which do not express HLA Class I and II molecules, for example, K562 cells, or cells in which nucleic acids encoding HLA and co-stimulatory molecules CD32, CD80, CD83, and 4-1BBL are injected into recombinant 293T cells genetically engineered so as not to express HLA Class I and II molecules, but is not limited thereto.

The term "co-stimulatory molecule" refers to a substance participating in the interaction between receptor-ligand pairs and T cells, which are expressed on the surface of antigen-presenting cells, and in order to induce the expression and proliferation of cytokine genes, two or more signals are required for resting T cells, the first signal is a signal imparting specificity and is produced by the interaction between an MHC/peptide complex and a TCR/CD3 complex, and the second signal is non-specific to antigen and refers to a "co-stimulatory" signal. The signal is known as an activity provided by bone-marrow-derived accessory cells such as macrophages and dendritic cells. The co-stimulatory molecules perform complete activation of CD8+ T cells by mediating co-stimulatory signals required under normal physiological conditions. In the present invention, a combination of CD32, CD80, CD83, and 4-1BBL is used as the co-stimulatory molecule.

The exosomes are secreted from artificial antigen-presenting cells prepared by selecting and introducing nucleic acids which encode HLA; and co-stimulatory molecules CD32, CD80, CD83, and 4-1BBL into cells which do not express HLA Class I and II molecules by using a known transformation technology, and thus may be isolated by centrifuging a cell culture broth. According to one embodiment, artificial antigen-presenting cells may be prepared by using K562 cells as the cells which do not express HLA Class I and II molecules and into which a vector into which nucleic acids encoding HLA and co-stimulatory molecules are inserted is introduced.

The nucleic acids encoding HLA and the co-stimulatory molecules are used in the broadest sense, and encompass single-stranded (ss) DNA, double-stranded (ds) DNA, cDNA, (−)-RNA, (+)-RNA, dsRNA, and the like. Preferably, the nucleic acid is double-stranded DNA.

Preferably, the HLA may be a human-derived nucleic acid sequence. For example, the HLA may be a base sequence set forth in SEQ ID NO: 1, but is not particularly limited thereto.

The CD80 may be a human- or mouse-derived nucleic acid sequence. For example, the CD80 may be a base sequence set forth in SEQ ID NO: 2, but is not particularly limited thereto.

The CD83 may be a human- or mouse-derived nucleic acid sequence, and may be, for example, a base sequence set forth in SEQ ID NO: 3, but is not particularly limited thereto.

The 4-1BBL may be a human- or mouse-derived nucleic acid sequence, and may be, for example, a base sequence set forth in SEQ ID NO: 4, but is not particularly limited thereto.

When a DNA is selected as the nucleic acid encoding HLA or the co-stimulatory molecule, the DNA may be used in a form in which the DNA is inserted into an expression vector.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (for example, bacterial vectors having a bacterial origin of replication and episomal mammalian vectors). Other vectors (for example, non-episomal mammalian vectors) are integrated into the genome of a host cell upon introduction into the host cell, and thereby are replicated along with the host genome. Moreover, certain vectors are capable of directing the expression of genes to which they are operably linked. As used herein, the vector refers to a "recombinant expression vector" (or simply, "expression vector"). In general, expression vectors useefulin recombinant DNA techniques are predominantly in the form of plasmids, and "plasmid" and "vector" may be used interchangeably as the plasmid is a type of vector most commonly used. However, the present invention also includes other types of expression vectors such as viral vectors providing an equivalent function (for example, an adenoviral vector, an adeno-associated viral (AAV) vector, a herpes viral vector, a retroviral vector, a lentiviral vector, and a baculoviral vector). Preferably, a lentiviral vector may be used. Transformation includes any method of introducing nucleic acids into organisms, cells, tissues or organs and may be performed by selecting a suitable standard technique depending on the type of host cell as known in the art. Examples of this method include electroporation, protoplast fusion, calcium phosphate ($CaPO_4$) precipitation, calcium chloride ($CaCl_2$)) precipitation, agitation by using silicon carbide fiber, agrobacterium-mediated transformation, and PEG, dextran sulfate, Lipofectamine, and the like, but are not limited thereto.

According to an embodiment of the present invention, artificial antigen-presenting cells may be produced by preparing each cDNA through PCR amplification for genes of human HLA-A2 and co-stimulatory molecules CD80, CD83, and 4-1BBL, inserting each cDNA into each lentiviral vector, and co-transducing these into K562 cells, and exosomes may be isolated by subjecting the cells to ultracentrifugation.

The exosome of the present invention stably expresses HLA and co-stimulatory molecules CD32, CD80, CD83, and 4-1BBL and expresses CD63, CD81, ICAM, CD9, CD63, and CD82 as typical markers of exosomes, but expresses FLOT-1, ALIX, EpCAM, ANNXA5, and TSG101 at low levels. These markers are not present in the cell membrane of K562 cells which are mother cells of the artificial antigen-presenting cells or are expressed at low levels.

Further, the exosome of the present invention may additionally express one or more selected from the group consisting of CD40L, CD70, and OX40L as a co-stimulatory molecule.

As used herein, "to sensitize an exosome with a substance" refers to reacting the exosome with the substance, and preferably refers to directly or indirectly presenting the substance on the surface of the exosome. As used herein, the substance refers to an antigen, and the "foreign antigen" is an antigen which the cell itself does not possess, and cells may be sensitized by delivery of the antigen thereto or contact with the antigen. As the delivery, it is possible to use electroporation, transfection, and the like by pulse energy without limitation. The contact may incubate an antigen and an exosome for a certain period of time.

For example, electroporation may use square wave pulses at a field strength of 100 to 150 volts/mm gap width for 2 to 10 ms (for example, 400 to 600 V for a gap of 4 mm), but may be appropriately adjusted at the level of a person with ordinary skill in the art.

As used herein, the term "antigen" is well known in the art, and includes not only all molecules capable of binding to antibodies, but also epitopes, peptide fragments of antigens capable of binding to MEW molecules, and immunogens. In the present invention, as the antigens, tumor antigens, pathogenic antigens, autoantibodies (normal or diseased), or the like are used, but the antigens is not limited thereto.

The tumor antigen refers to an antigen associated with tumors as a tumor associated antigen (TAA). Examples of well-known TAAs include ovalbumin, survivin, gp75, gp1OO, MDM2, MART-1, MAGE-1, MAGE-3, tyrosinase, telomerase, her-2/neu, α-1 fetoprotein, G250, NY-ESO-1, and the like. Sequences of some peptides fragments of the TAA binding to MHC molecules include $Ova_{257}$ (SIINFEKL: SEQ ID NO: 9), tyrosinase-related protein $1_{455}$ ($Trp1_{455}$; TAPDNLGYA: SEQ ID NO: 10), $Trp2_{180}$ (SVYDFFVWL: SEQ ID NO: 11), and $gp100_{25}$ (gp10025; EGSRNQDWL: SEQ ID NO: 12), a MAGE 1 nonapeptide (EADPTGHSY: SEQ ID NO: 13), a MART-APL peptide (LAGIGILTV: SEQ ID NO: 14), a natural peptide (AAGIGILTV: SEQ ID NO: 15) or a PSA-1 peptide (FLTPKKLQCV: SEQ ID NO: 16), and the like. Additional sequences of the tumor associated peptides and antigens are known to those skilled in the art.

Examples of tumors associated with the tumor antigen include a solid tumor, a liquid tumor, hematologic tumor, renal cell cancer, melanoma, breast cancer, prostate cancer, testicular cancer, bladder cancer, ovarian cancer, cervical cancer, stomach cancer, esophageal cancer, pancreatic cancer, lung cancer, neuroblastoma, glioblastoma, retinoblastoma, leukemia, myeloma, lymphoma, hepatoma, adenocarcinoma, sarcoma, a malignant tumor (carcinoma), blastoma, and the like.

The pathogen antigen refers to any organism or virus causing a disease and also to attenuated derivatives thereof. The term "pathogen" refers to any virus or organism which is involved in the etiology of a disease and also to attenuated derivatives thereof. Such pathogens include bacteria, protozoan, fungal and viral pathogens, for example, *Helicobacter* sp., for example, *Helicobacter pylori, Salmonella* sp., *Shigella* sp., *Enterobacter* sp., *Campylobacter* sp., various mycobacteria, for example, *Mycobacterium leprae, Mycobacterium tuberculosis, Bacillus anthracis, Yersinia pestis, Francisella tularensis, Brucella* sp., *Leptospira interrogans, Staphylococcus* sp., for example, *S. aureus, Streptococcus* sp., *Clostridum* sp., *Candida albicans, Plasmodium* sp., *Leishmania* sp., *Trypanosoma* sp., human immunodeficiency virus (HIV), hepatitis C virus (HCV), human papilloma virus (HPV), cytomegalovirus (CMV), HTLV, herpes virus (for example, herpes simplex virus type 1, herpes simplex virus type 2, coronavirus, varicella-zoster virus, and Epstein-Barr virus), papilloma virus, influenza virus, hepatitis B virus, poliomyelitis virus, measles virus; mumps virus, or rubella virus, but are not limited thereto.

Examples of the autoantibody include an anti-nuclear antibody, an anti-γ-globulin antibody, an antibody against an autoblood component, or an antibody against an autoorgan, but are not particularly limited thereto. When the autoantibody is used as a foreign antigen, the CD4 T cell vaccine may induce strong anti-tumor immunity, and, thus, it can be effective in overcoming potential immunological tolerance to a self-antigen expressed in normal tissue.

The exosomes sensitized with the antigen of the present invention are characterized in that the exosomes induce proliferation of antigen-specific CD8+ T cells and directly stimulate CD8+ T cells, or when K562 cells and the exosome are washed after being co-cultured, and then treated with the antigen, co-stimulatory molecules and HLA expressed from the exosome are delivered to K562 cells, and the K562 cells may stimulate CD8+ T cells, and thus may indirectly stimulate CD8+ T cells by delivering a surface substance to other cells.

The stimulation of CD8+ T cells by the exosome is similar to the level of that of dendritic cells.

Since the exosome of the present invention is sensitized with a foreign antigen while overexpressing co-stimulatory molecules to improve an antigen-specific T cell response, the exosome is effective in treating tumors, pathogen infections, or autoimmune diseases according to the type of foreign antigen.

Accordingly, the present invention provides an immunotherapeutic agent including the exosome.

The immunotherapeutic agent according to the present invention may increase an immune response or selectively elevate a portion of the immune response preferred for the treatment or prevention of a specific disease, infection or disorder.

Based on this, the present invention provides a vaccine for preventing tumors, pathogen infections, or autoimmune diseases, or a pharmaceutical composition for treating tumors, pathogen infections, or autoimmune diseases, including the exosome.

For example, examples of the tumor include a renal cell tumor, melanoma, chronic lymphocytic leukemia, breast cancer, lung cancer, prostate cancer, ovarian cancer, colorectal cancer, or the like, but are not particularly limited thereto.

Preferred examples of the pathogen infection include HIV, HCV, and the like, but are not particularly limited.

Preferred examples of the autoimmune disease include systemic lupus erythmatosus (SLE), rheumatoid arthritis (RA), rheumatoid fever, and the like, but are not particularly limited thereto.

The vaccine of the present invention may include all immunization methods performed by single administration and immunization methods performed by continuous administration.

The pharmaceutical composition may include an active ingredient with an active or inert pharmaceutically acceptable carrier, making the composition suitable for diagnostic or therapeutic use in vitro, in vivo or ex vivo.

The pharmaceutically acceptable carrier includes any pharmaceutical carrier compatible with T cells, such as a phosphate buffered saline solution and a protein excipient including serum albumin such as human serum albumin (HSA), recombinant human albumin (rHA), gelatin, casein, and the like. For examples of carriers, stabilizers and adjuvants, refer to Martin REMINGTON'S PHARM. SCI, 18th Ed. (Mack Publ. Co., Easton (1995)) and the "PHYSICIAN'S DESK REFERENCE", 58nd Ed., Medical Economics, Montvale, N.J. (2004). The term "carrier" may include a buffer or a pH adjusting agent, and typically, the buffer is a salt prepared from an organic acid or base. A representative buffer includes organic acid salts such as salts of citric acid, salts of ascorbic acid, salts of gluconic acid, salts of carbonic acid, salts of tartaric acid, salts of succinic acid, salts of acetic acid, or salts of phthalic acid; Tris, tromethamine hydrochloride, or phosphate buffers. Additional carriers include a polymeric excipient/additive such as polyvinylpyrrolidone, Ficoll (a polymeric sugar), a dextrate (for example, cyclodextrin, for example, 2-hydroxypropyl-quadrature,-cyclodextrin), polyethylene glycol, an antioxidant, an antistatic agent, a surfactant (for example, a polysorbate such as "TWEEN 20" and "TWEEN 80"), a lipid (for example, phospholipid, fatty acid), a steroid (for example, cholesterol), and a chelating agent (for example, EDTA). Agents for preventing or reducing ice formation may be included.

The pharmaceutical composition of the present invention may be prepared in various formulations as appropriate. For example, a formulation suitable for parenteral administration, such as by intratumoral, intraarterial (in the joints), intravenous, intramuscular, intradermal, intraperitoneal, intranodal and subcutaneous routes, and carriers include an antioxidant, a buffer, a bacteriostat, and a solute that renders the formulation isotonic with the blood of an intended recipient, and an aqueous and non-aqueous sterile suspension that may include a suspending agent, a solubilizer, a thickening agent, a stabilizer, and a preservative. Intravenous or intraperitoneal administration is a preferred method. The dose of cells administered to a subject is in an amount, effective to achieve a desired beneficial therapeutic response in the subject over time, or to inhibit growth of cancer cells, or to inhibit infection. For example, the administration may be performed by a method of obtaining and storing a blood sample from a subject prior to infusion and by using the blood samples for subsequent analysis and comparison. In general, at least about $1 \times 10^4$ to $1 \times 10^6$ and typically, $1 \times 10^8$ to $1 \times 10^{10}$ cells may be infused intravenously or intraperitoneally into a 70 kg patient over roughly 60 to 120 minutes. For administration, cells of the present invention are administered at a rate determined by the LD-50 (or other methods of measuring toxicity) according to the cell type and the side-effects according to the cell type at various concentrations, in consideration of the overall health status and body weight of the subject. Administration may be accomplished via single or divided doses. The exosome of the present invention may supplement other treatments for a specific condition by using a known conventional therapeutic method including a cytotoxic agent, a nucleotide analog and a biologic response modifier. Similarly, the biological response modifier may be optionally added to treatment by the exosome of the present invention.

Further, the present invention provides a method for proliferating T cells, the method including a step of co-culturing the exosome and any one T cell of a CD4 T cell, a CD8 T cell, or a γδT cell.

The present invention also provides a method for preparing cytotoxic T cells in vitro, the method including a step of stimulating any one of a CD4 T cell, a CD8 T cell, or a γδT cell with the exosome sensitized with one or more antigens selected from the group consisting of a tumor antigen, a pathogen antigen, and an autoantibody.

The exosome of the present invention may proliferate the T cells when co-cultured with the CD4 T cell, the CD8 T cell, or the γδT cell. In addition, when the T cells are stimulated by an exosome sensitized with an antigen, antigen-specific cytotoxic T cells may be produced.

The stimulation or co-culturing of the CD4 T cell, the CD8 T cell, or the γδT cell by or with the exosome is performed in a cell culture medium supplemented with Interleukin-2 (IL-2) in the absence of an immunostimulatory ligand.

The cell culture medium may be a safe medium for animal cell culture. Examples of the safe medium include Dulbecco's Modified Eagle's Medium (DMEM), Minimal Essential Medium (MEM), Basal Medium Eagle (BME), RPMI1640, F-10, F-12, α-Minimal Essential Medium (α-MEM), Glasgow's Minimal Essential Medium (GMEM), Iscove's Modified Dulbecco's Medium, and the like, but are not limited thereto.

The IL-2 may be added at a concentration of 20 to 100 IU/mL.

The stimulation by using the exosome may be performed for 4 days to 10 days, but is not particularly limited thereto.

The culture conditions may be performed at a flow rate amount of 5 to 15% carbon dioxide and at 35 to 37° C. in a $CO_2$ incubator, but are not particularly limited thereto.

Hereinafter, the present invention will be described in more detail through the Examples according to the present invention, but the scope of the present invention is not limited by the Examples suggested below.

EXAMPLES

<Example 1> Preparation of Exosome (Cells)

The use of human materials was reviewed and approved by the Institutional Review Board of College of Medicine of the Catholic University of Korea. PBLs were collected from healthy volunteers by using Ficoll-Hypaque (GE Healthcare, Pittsburgh, Pa., USA). K562 cell lines were obtained from the American Type Culture Collection (Manassas, Va., USA). All of the cell lines were cultured as recommended by the provider.

(Establishment of Artificial APCs)

HLA-A2, CD80, 4-1BBL, and CD83 cDNA were individually cloned into a pcDNA 3.1 vector (Invitrogen, Carlsbad, Calif., USA) and sequentially transfected into K562 cells by using the Nucleofector Kit (Lonza, Basel, Switzerland), according to the manufacturer's instructions.

K 562 cells were transfected with pcDNA3-CD32, capable of being loaded with anti-CD3 antibodies to produce KEX. Moreover, K562 cells were transfected with 4-1BBL, CD80, and CD83 to produce CoEX, respectively. Here, CoEX-A2 was further produced by further transfection of HLA-A2. Stable transfectants were selected by using 1 mg/ml G418 and FACS cell sorting by each antibody staining.

(Isolation and Culturing of CD8+ T Cells)

Human peripheral blood was obtained from 5 healthy HLA-A2 volunteers and mononuclear cells were isolated by using Ficoll-Hypaque (Amersham Pharmacia Biotech, Piscataway, N.J., USA) density gradient centrifugation. The HLA-A subtypes of the volunteers were determined by sequence-based typing in an HLA laboratory. Consent forms and approval for this study were obtained from the volunteers and the Institutional Review Board of College of Medicine of the Catholic University of Korea. Following density separation, CD8+ T cells (purity: up to 95%) were isolated by using MACS isolation kits (Miltenyi Biotec, Bergisch Gladbach, Germany).

(Culturing and Antigen Pulsing of Dendritic Cells)

Immature DCs were produced from CD14+ monocytes by culturing in a RPMI 1640 medium supplemented with 10% fetal bovine serum, 100 ng/mL of GM-CSF (GM-CSF; Endogen, Woburn, Mass., USA), and 50 ng/mL of IL-4 (IL-4; Genzyme, Cambridge, Mass., USA) in a humidified incubator at 37° C. with 5% $CO_2$ while exchanging the media every 3 days for 6 to 7 days. Immature DCs were harvested and then infected with Adv-survivin with a MOI of 500 and/or a recombinant pp65 protein of 2 L/$10^6$ DCs (Miltenyi Biotec, Bergisch Gladbach, Germany) at 37° C. for 3 hours. After antigen loading, DCs were matured for 24 hours by 100 ng/mL of TNF-α and 100 ng/mL of LPS.

(Exosome Purification and Antibody Array)

The procedure for exosome isolation was based on a previously disclosed exosome purification method using ultracentrifugation (*Current Protocols in Cell Biology* (2006) 3.22.1-3.22.29). When cells reached 90% confluency, the media were exchanged, and cultured after 72 hours, and then the supernatants were collected. The collected supernatants were centrifuged at 500 g for 10 minutes to remove cell debris. The clarified supernatant was concentrated to a volume of 500 mL by centrifugation for 10 minutes, filtered through a 0.22 mm filter and then centrifuged at 100,000 g for 1 hour and 30 minutes. The exosomal pellet at the bottom of centrifugal tube was washed and eluted with PBS. Finally, the content of exosomal protein was determined by using the bicinchoninic acid (BCA) assay and NanoDrop ND-1000 (NanoDrop Technologies, Montchanin, Del., USA).

Known exosomal markers were detected by using the Exo-Check antibody array (System Biosciences, Mountain View, Calif.). Briefly, exosomal protein lysates were prepared by adding 600 μL of an exosome lysis buffer to 300 μg of exosomal protein. The antibody membrane array was placed in distilled water at room temperature for 2 minutes. Exosomal lysate/binding mixture was added to the antibody membrane and then incubated on a shaker at 41° C. overnight. After washing with an array wash buffer, a detection buffer was added to the membrane and incubated at room temperature for 2 hours. The final signal was analyzed by washing the membrane twice with the wash buffer, developing the membrane, and then exposing the membrane.

(Flow Cytometry)

1) Surface Marker Analysis

Exosomes were coupled to the following modified beads as previously disclosed (Thery, C et al. *Journal of immunology*, vol. 166, pp. 7309-'7318, 2001). Purified exosomes (30 μg) were incubated with 4-mm diameter aldehyde/sulfate latex beads (Interfacial Dynamics, Portland, Oreg.) for 15 minutes at room temperature. Subsequently, the exosomes were diluted with PBS, and the coupling reaction was continued for an additional 2 hours. The reaction was stopped by adding 100 mM glycine thereto. Coated beads were washed three times in PBS and stained with specific antibodies. The following fluorescence-conjugated antibodies were used to examine the surface expression of co-stimulatory molecules or exosomal markers: aCD9(SN4 C3 3A2), aCD63(H5C6), aCD82(ASL-24), a4-1BBL(5F4), aCD83(HB15e), aCD80(2D10), and HLA-A2(BB7.2). All antibodies were purchased from BioLegend (San Diego, Calif., USA). In brief, $1 \times 10^6$ viable T cells were washed twice with PBS containing 2% fetal bovine serum and incubated with 0.5 mg of the associated antibodies for 20 minutes.

2) CD8+ T Cell Proliferation Assays

CFSE-labeled CD8+ T cells were stimulated by the presence of 50 μg/mL of CoEX-A2, CoEX, KEX-A2, and KEX for 130 hours. After stimulation for 130 hours, cells were harvested and stained with a PE-anti-human CD8 antibody. The stained cells were applied to FACScanto II. Data were analyzed using ModFIT LT software (Verity Software House Inc., Topsham, Me.).

3) Cytotoxicity Testing

After antigen pulsing, DEX or CoEX-A2 was cultured with CD8+ T cells. CD8+ T cells purified to a final concentration of $2.0 \times 10^6$/well in a 24-well plate and DEX or CoEX-A2 were co-cultured in a RPMI 1640 supplemented with 10% fetal bovine serum (Gibco-BRL), 2 mM L-glutamine, and 1% penicillin-streptomycin (Cambrex). On day 7, the cells were harvested for re-stimulation. 20 U/mL IL-2 (Endogen) was added to the wells every 3 days, beginning on day 8. After 3 rounds of stimulation, the T cells were evaluated for antigen-specific immune responses. Expanded CD8+ T cells were evaluated by staining with 7-AAD after 6 hours of post cultivation under the indicated experimental conditions using 100 μg CoEX-A2 or DEX in the presence of 20 IU/mL IL-2. Data were analyzed using FlowJo software (Tree Star, Otlen, Switzerland).

(ELISPOT Assay)

For ELISPOT assays, $5 \times 10^4$ CD8+ T cells were added to each well of MultiScreen hemagglutinin plates (Millipore, Bedford, Mass.) that were pre-coated with one among anti-IFN-γ (6 μg/mL) capture antibodies. After 48 hours of incubation, culture plates were washed with an excess of PBS_0.1% Tween 20, a detection antibody was added to the anti-IFN-γ (6 μg/mL) capture antibody, and the plates were incubated at 4° C. for 24 hours. After washing, streptavidin-horseradish peroxidase (1:1,000) was added thereto, and the plates were incubated at room temperature for 2 hours. The plates were washed and developed using the peroxidase substrate 3-amino-9-ethylcarbazole (Sigma, Deisenhofen, Germany). Spots were counted in an ELISPOT Reader (AID Elispot, Strassberg, Germany). To estimate the number of antigen-responsive T cells, the number of spots in wells containing no antigen (background) was subtracted from those of the experimental wells. For detection of cells secreting IFN-g, ELISPOT assays were performed using a BD Elispot assay kit (BD Biosciences), and the procedure was performed according to the manufacturer's instructions.

Peptides restricted to HLA-A2, $pp65_{495-503}$ (NLVPMVATV: SEQ ID NO: 5), $MP1_{159-167}$ (YLQQNWWTL: SEQ ID NO: 6), $MART1_{26-35}$ (ELAGI-GILTV: SEQ ID NO: 7), and $WT1_{126-134}$ (RMFPNAPYL: SEQ ID NO: 8) were synthesized by AnyGen Co. Ltd. (Gwangju, South Korea). Briefly, T cells were pulsed repeatedly three times with 10 g/mL of pp65, LMP1, MART1, and WT1 peptides at a ratio of 10:1, or incubated with unpulsed T2 cells. The number of spots corresponding to IFN-γ-secreting cells was counted using AID-ELISPOT Reader.

(Statistical Analysis)

The results are expressed as mean±SEM. Statistical significance was determined by the Student t test or by two-way ANOVA, followed by the Tukey post hoc test to analyze clinical scores. Statistical significance was accepted at $p<0.05$.

Figure 1B:
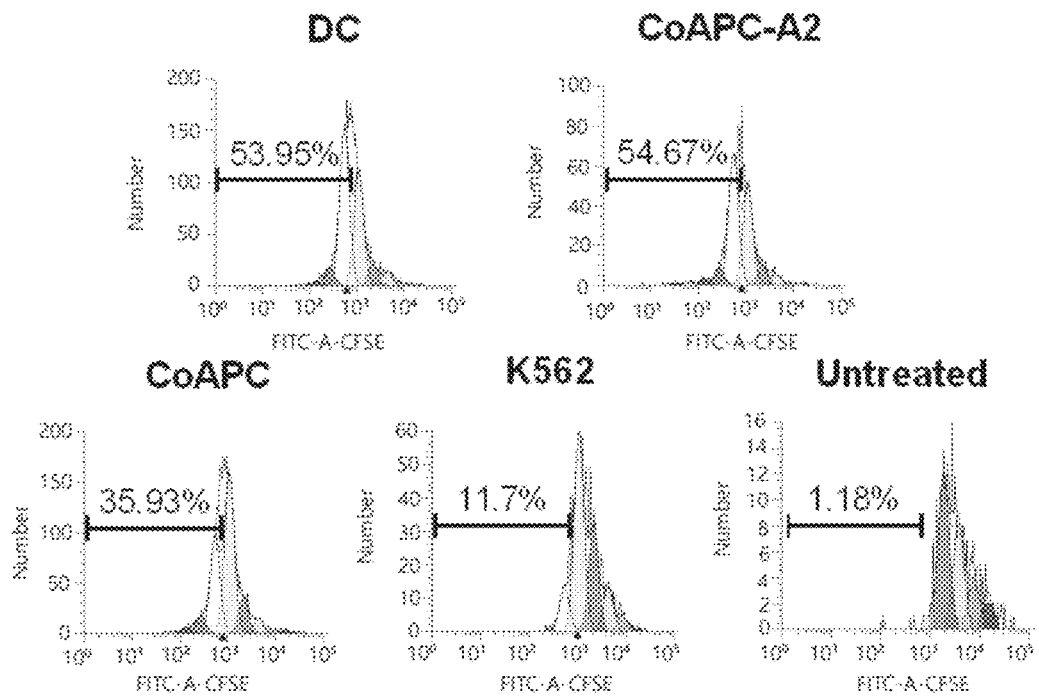

<Experimental Example 1> Characterization of Exosomes Derived from Genetically Engineered K562 Cells As illustrated in FIG. 1a, genetically engineered K562 cells stably express various co-stimulatory molecules such as CD80, CD83, and CD137L (4-1BBL), CD32, and HLA-A2 genes. When genetically engineered K562 cells were treated with pp65, CD8 T cells were stimulated, and then analysis by CFSE was performed, proliferation of viral antigen-specific cells can be induced 5 days after culture (FIG. 1b).

In order to isolate exosomes from a culture solution in which various co-stimulatory molecules and HLA-A2 genes were expressed and confirm the exosomes, CD81, ICAM, CD63, ALIX, TSG101, EpCAM, and FLOT-1 as a positive control and CD9, CD63, and CD82 were analyzed by a Western blot method and a flow cytometry method, respectively. GM130 expressed in Golgi was used as a negative control.

Figure 1C:
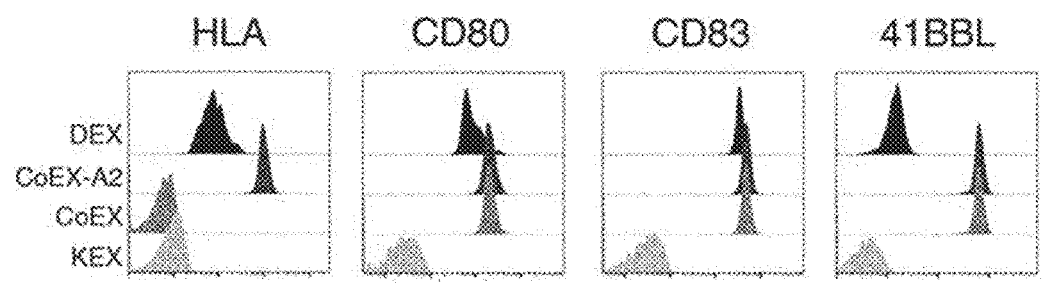
Figure 1D:
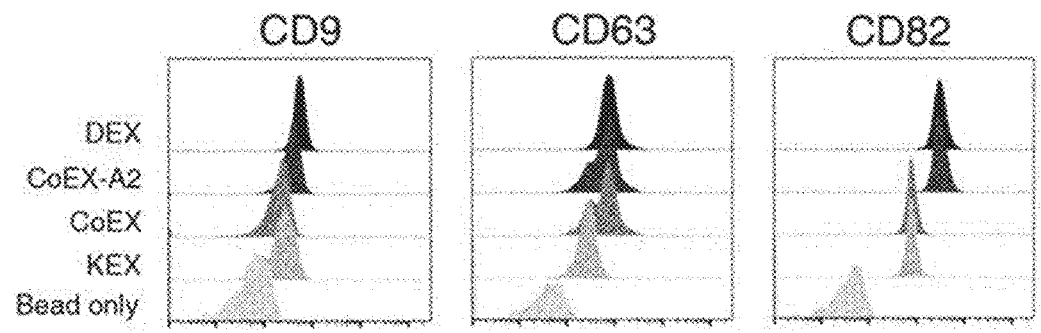
Figure 1E:
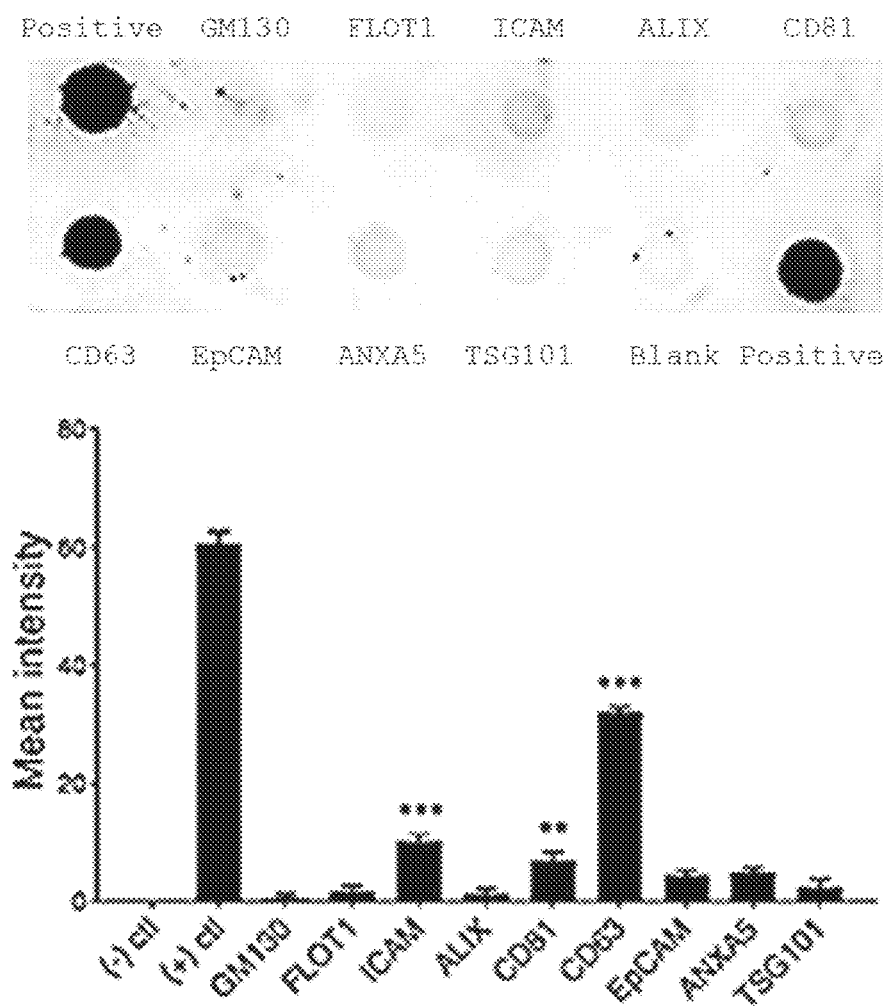

As a result of the experiment, CoEX-A2 included HLA-A2, CD80, CD83, and 4-1BBL at detectable levels (FIG. 1c). Further, CoEX-A2 included typical exosomal marker proteins CD9, CD63, and CD82, but these markers were not present in the cell membrane of K562 cells, or were expressed at low levels (FIG. 1d). Finally, the exosome CoEX-A2 was positive for CD63, CD81, and ICAM, but FLOT-1, ALIX, EpCAM, ANNXA5, and TSG101 were expressed at low levels (FIG. 1e).

Figure 2A:
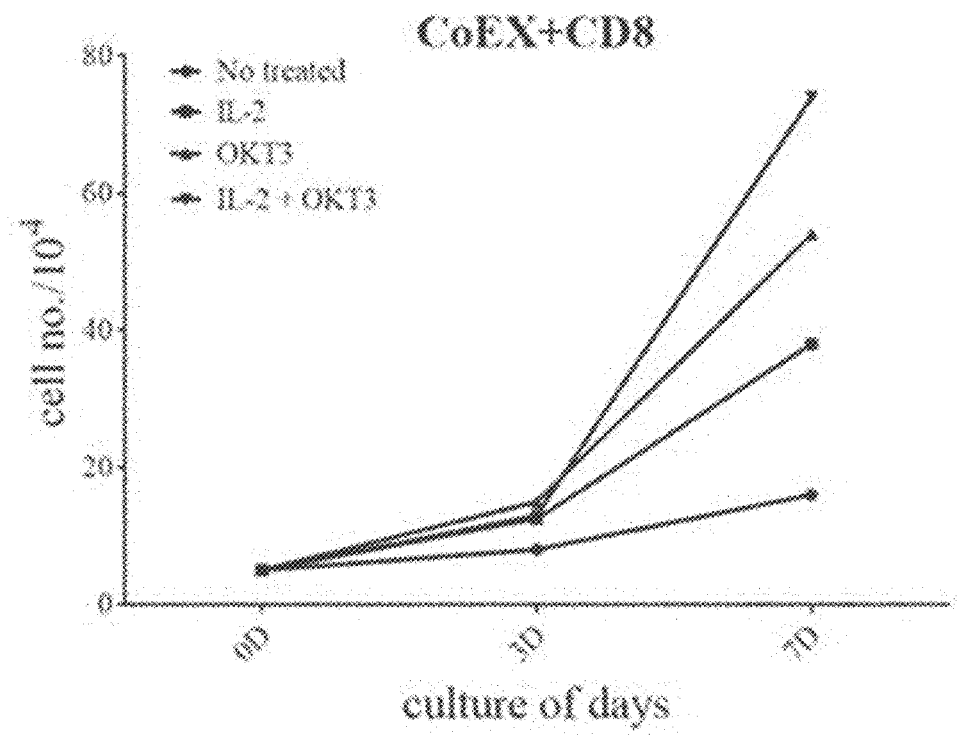
FIG. 2a illustrates cell proliferation results measured after mixing CoEX or KEX with CD8+ T cells at a ratio of 1:2 in the presence and absence of an anti-CD3 antibody (hOKT3, 0.5 μg/mL) and stimulating the mixture with OKT3 and IL-2 for 16 hours.
Figure 2A:
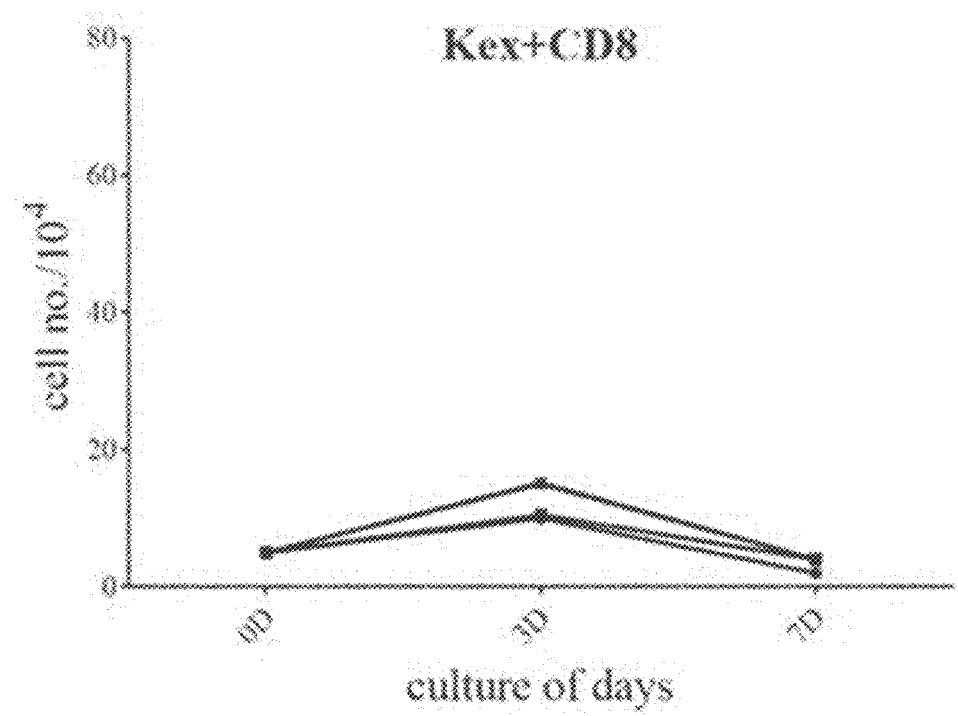
Figure 2B:
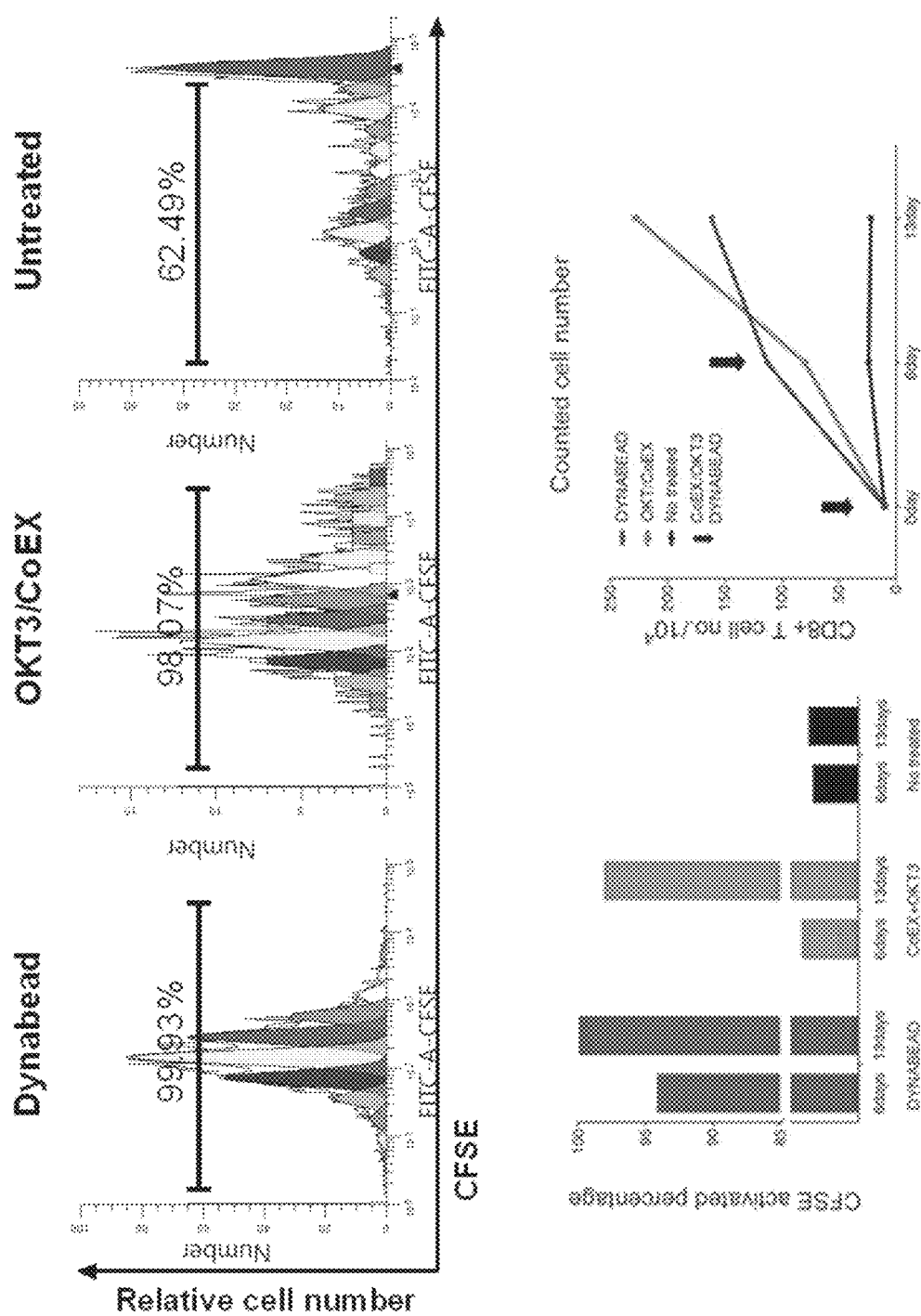
FIG. 2b illustrates flow cytometry histograms illustrating results compared with DYNBEAD including CD3 and a co-stimulatory molecule CD28, and additionally illustrates the intensity of CFSE-labeled cells analyzed by ModFit LT 3.0 software as a representative staining result in three independent experiments.

<Experimental Example 2> Immunostimulatory Response Confirmation of Genetically Engineered Exosomes K 562 cells were transfected with pcDNA3-CD32, capable of being loaded with anti-CD3 antibodies to produce CoEX. The first visible event in T cell activation is the formation of clusters between CoEX and CD8+ T cells. To assay for cluster formation, CD8+ T cells were cultured in the presence or absence of soluble anti-CD3 antibodies, IL-2, and CoEX. Mixtures of CoEX and CD8+ T cells remained free of clusters in the absence of anti-CD3 antibodies, but large clusters in mixtures of CoEX and CD8+ T cells were observed in the presence of anti-CD3 antibodies (not shown). Further, these clusters grew in size for 8 hours to 12 hours. This effect of CoEX on the proliferation of cultured CD8+ T cells was enhanced by incubation with OKT3 and IL-2. In addition, optimal proliferation of these cells was observed in the presence of OKT3, IL-2, and CoEX, except for KEX (FIG. 2a). Furthermore, to confirm the degree of effect of CoEX, the effect was compared with that of DYNABEAD including CD3 and a co-stimulatory molecule CD28, and it was observed that CFSE-labeled CD8+ T cells were activated at similar levels in both groups, and the proliferation degree of cells was also significantly increased (FIG. 2b).

Figure 3:
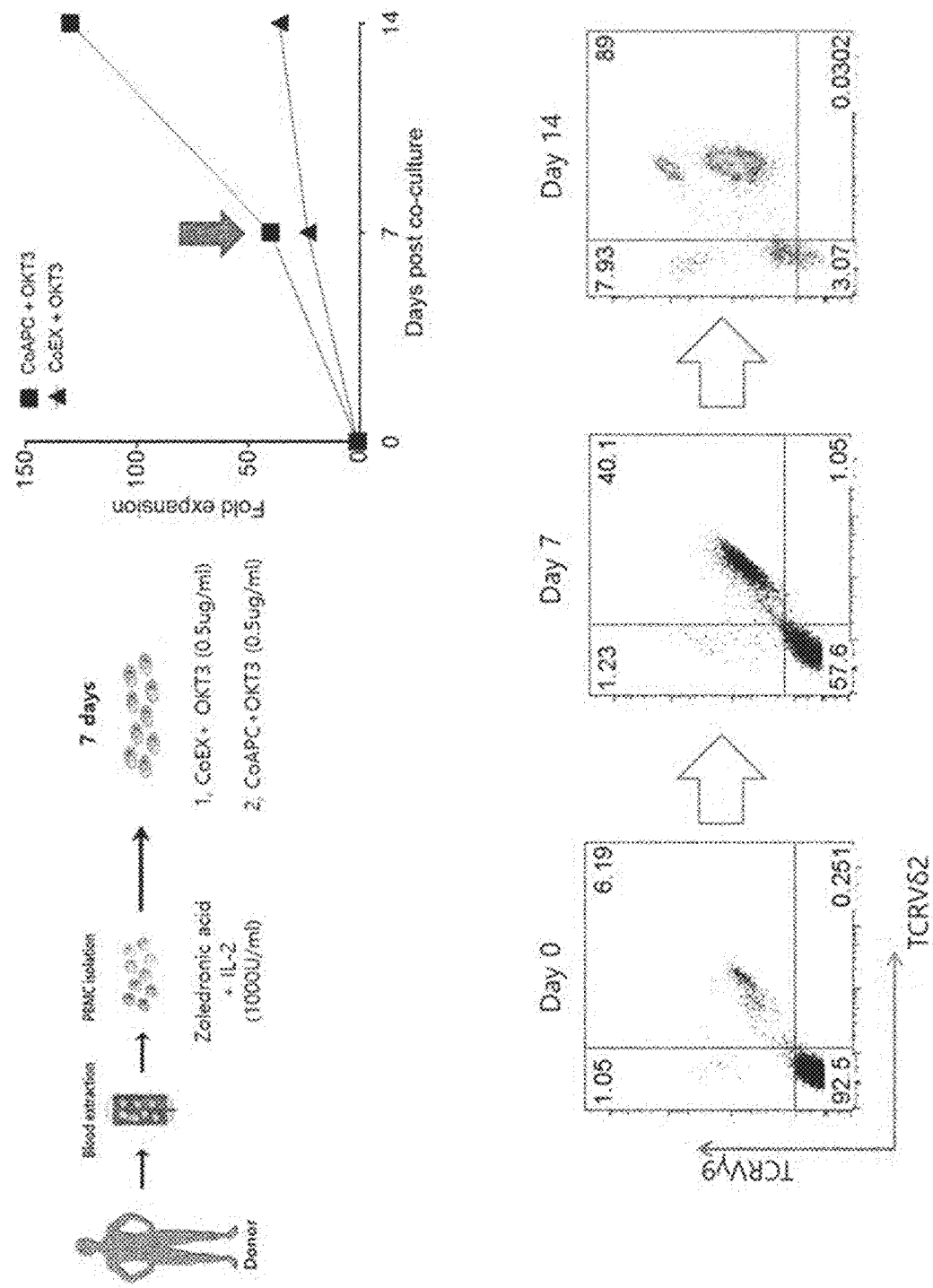
FIG. 3 illustrates a procedural view (left view) of stimulating γδT cells for 14 days, a result of proliferating γδT cells (right view), and a flow cytometry analysis result of Vγ9+/Vδ2+T (bottom view) by treating human peripheral blood with zoledronic acid and IL-2 (1000 IU/mL) for 7 days to increase the number of γδT cells, and then using CoEX or feeder cells CoAPC and OKT3 (0.5 μg/mL) from Day 7.

According to the stimulation procedural view disclosed in the left side view of FIG. 3, after the number of γδT cells was increased by treating human peripheral blood with zoledronic acid and IL-2 (1000 IU/mL) for 7 days, γδT cells were stimulated for 14 days by using CoEX or feeder cells CoAPC and OKT3 (0.5 μg/mL) from Day 7.

As illustrated in the right side view of FIG. 3, CoEX may proliferate γδT cells at the one-third fold level of CoAPC.

As illustrated in the bottom side view of FIG. 3, it was confirmed that when CoEX was used, the purity of Vγ9+/Vδ2+ T cells was increased with the passage of culture time.

Figure 4A:
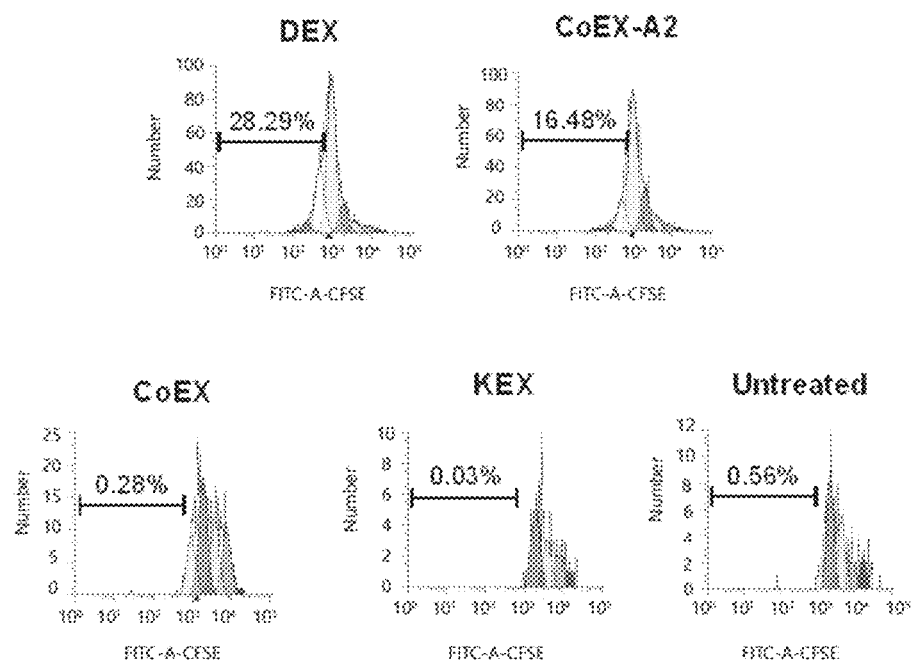
FIG. 4a illustrates that CD8+ T cells are measured by flow cytometry after the CD8+ T cells are incubated with an exosome, analyzed in the presence (+) or absence (−) of a CMV peptide, and incubated with exosomes including HLA-A2/co-stimulatory molecules or including no HLA-A2/co-stimulatory molecules for 130 hours, and additionally illustrates the intensity of CFSE-labeled cells analyzed by ModFit LT 3.0 software as a representative staining result in three independent experiments.

CoEX-A2 stimulated pp65-specific CD8+ T cells at a level similar to that of DEX. In contrast, an exosome (KEX) isolated from K562 cells, an exosome (CoEX) expressing only co-stimulatory molecules, and an exosome (KEX-A2) expressing only HLA-A2 did not exhibit a significant level of immunostimulatory response (FIG. 4a).

Figure 4B:
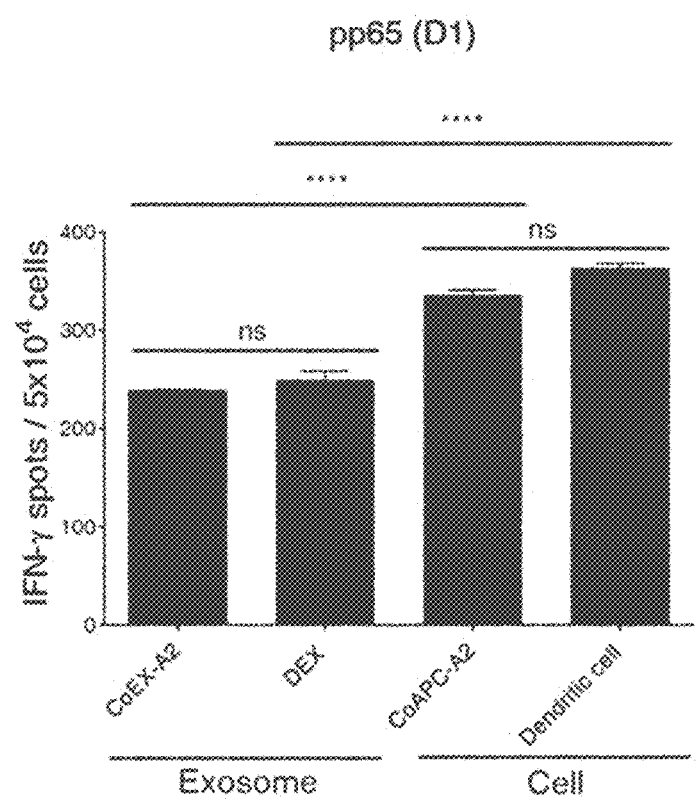
FIG. 4b illustrates ELISPOT analysis results of stimulating CD8+ T cells ($5 \times 10^5$) isolated from human peripheral blood mononuclear cells (PBMCs) by using exosomes (CoEX-A2, DEX) and antigen-presenting cells (CoAPC-A2, dendritic cell) in the presence or absence of a pp65 peptide.

Similarly, CoEX-A2 exhibited significant stimulation of CD8+ T cells at a level similar to that of DEX in a proliferation analysis using the CFSE dilution method, unlike the other exosome groups (FIG. 4b).

To find a suitable concentration of CoEX-A2 for stimulation of viral peptide-specific CD8+ T cells, CoEX-A2 was cultured with CD8+ T cells in the presence of a pp65 peptide.

Figure 5:
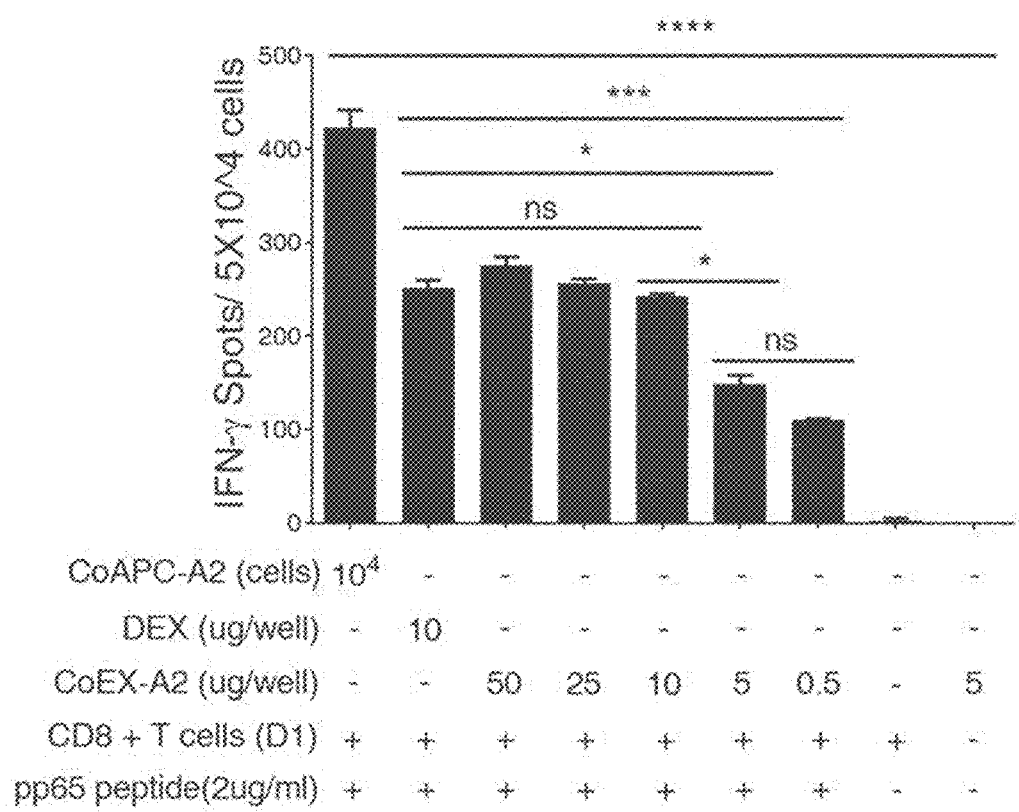
FIG. 5 illustrates ELISPOT analysis results showing the stimulation of naive CD8+ T cells by using a peptide-loaded exosome (CoEX-A2) which expresses HLA-A2 and co-stimulatory molecules. An exosome pre-loaded with a viral peptide induces the dose-dependent stimulation of CD8+ T cells. The K562 cell which expresses HLA-A2 and co-stimulatory molecules was used as a positive control.

As illustrated in FIG. 5, CoEX-A2 induced similar levels of CD8+ T cell stimulation at 50 μg/mL and 5 μg/mL, but at 0.5 μg/mL, the frequency of IFN-γ-secreting T cells was even lower. Further, treatment with CoEX-A2 exhibited an even lower level of stimulatory activity than engineered K562 cells. From these results, 5 μg/mL was selected as a concentration of exosomes for the subsequent experiments.

T cell stimulation responses were confirmed by treating CD8+ T cells obtained from 5 volunteers expressing HLA-A2 and two volunteers expressing no HLA-A2 with CoEX-A2.

Figure 6:
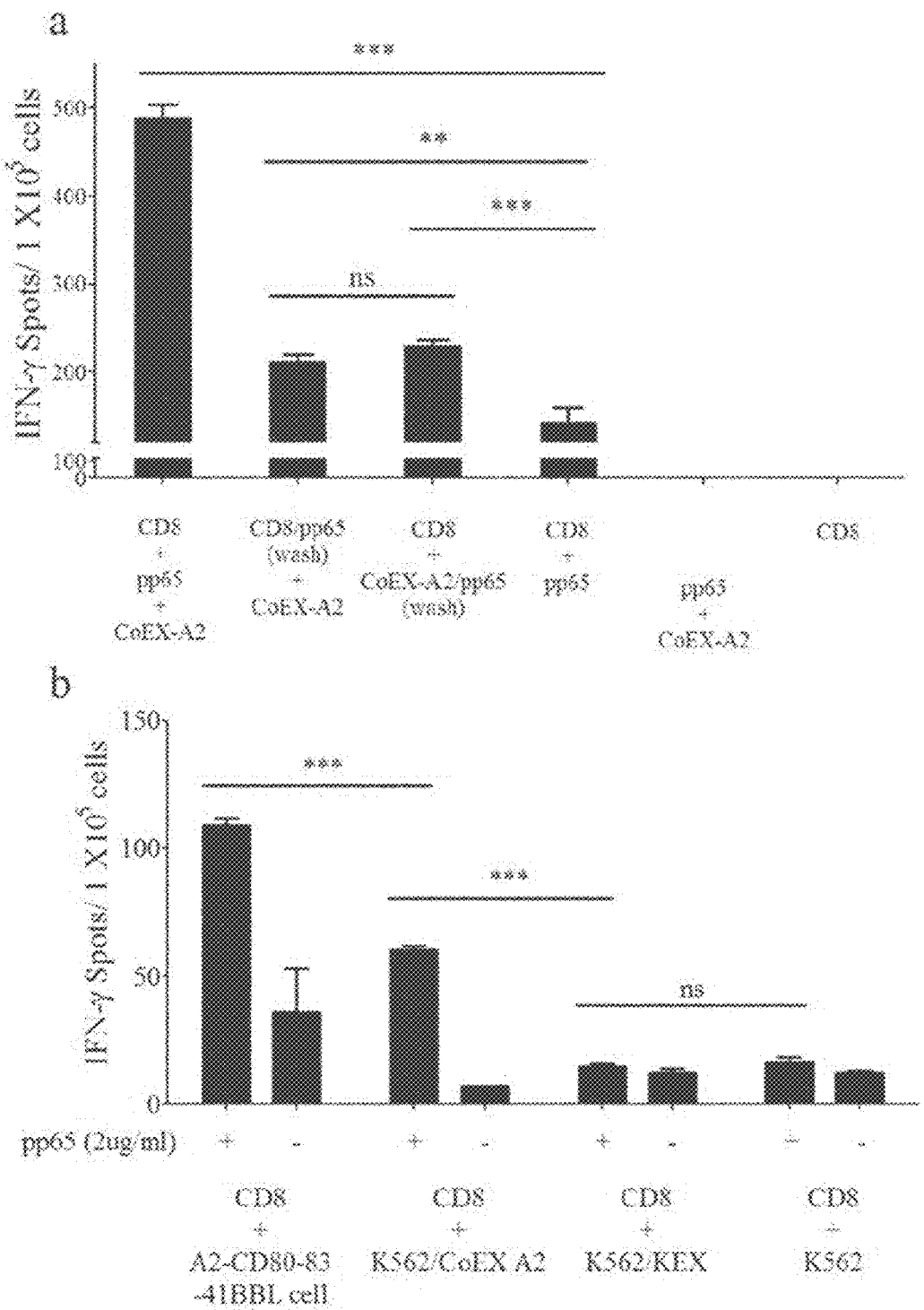
FIG. 6 illustrates an inter-donor comparison of IFN-γ secretion and expression by human CD8+ T cells treated with virus or tumor antigen-loaded exosomes.

As illustrated in FIGS. 6A and 6B, as a result of stimulation with $pp65_{495-503}$ (NLVPMVATV: SEQ ID NO: 5) and $MART1_{26-35}$ (ELAGIGILTV: SEQ ID NO: 7) peptides restricted to HLA-A2, cells harvested from healthy volunteers expressing HLA-A2 produced pp65-specific CD8+ T cells and MART-1-specific CD8+ T cells at the number of 100 or more and less than 100 per $10^5$ cells, respectively. Meanwhile, there was no response in the healthy volunteer sample expressing no HLA-A2. Therefore, the proliferation of antigen-specific CD8+ T cells was confirmed using both viral antigens and tumor antigens, as restricted to HLA-A2.

<Experimental Example 3> Direct and Indirect Antigen Presentation and Co-Stimulatory Transfer of CoEX-A2

In order to confirm direct and indirect stimulation responses of CoEX-A2 to pp65-specific CD8+ T cells, experiments were carried out by setting Group 1 (CD8, pp65, and CoEX-A2 mixed at one time), Group 2 (pp65 was put in CD8 and washed, followed by treatment with CoEX-A2), Group 3 (CoEX-A2 treated with pp65, washed and CD8+ T cells treated), and Group 4 (CD8 treated with only pp65).

Figure 7:
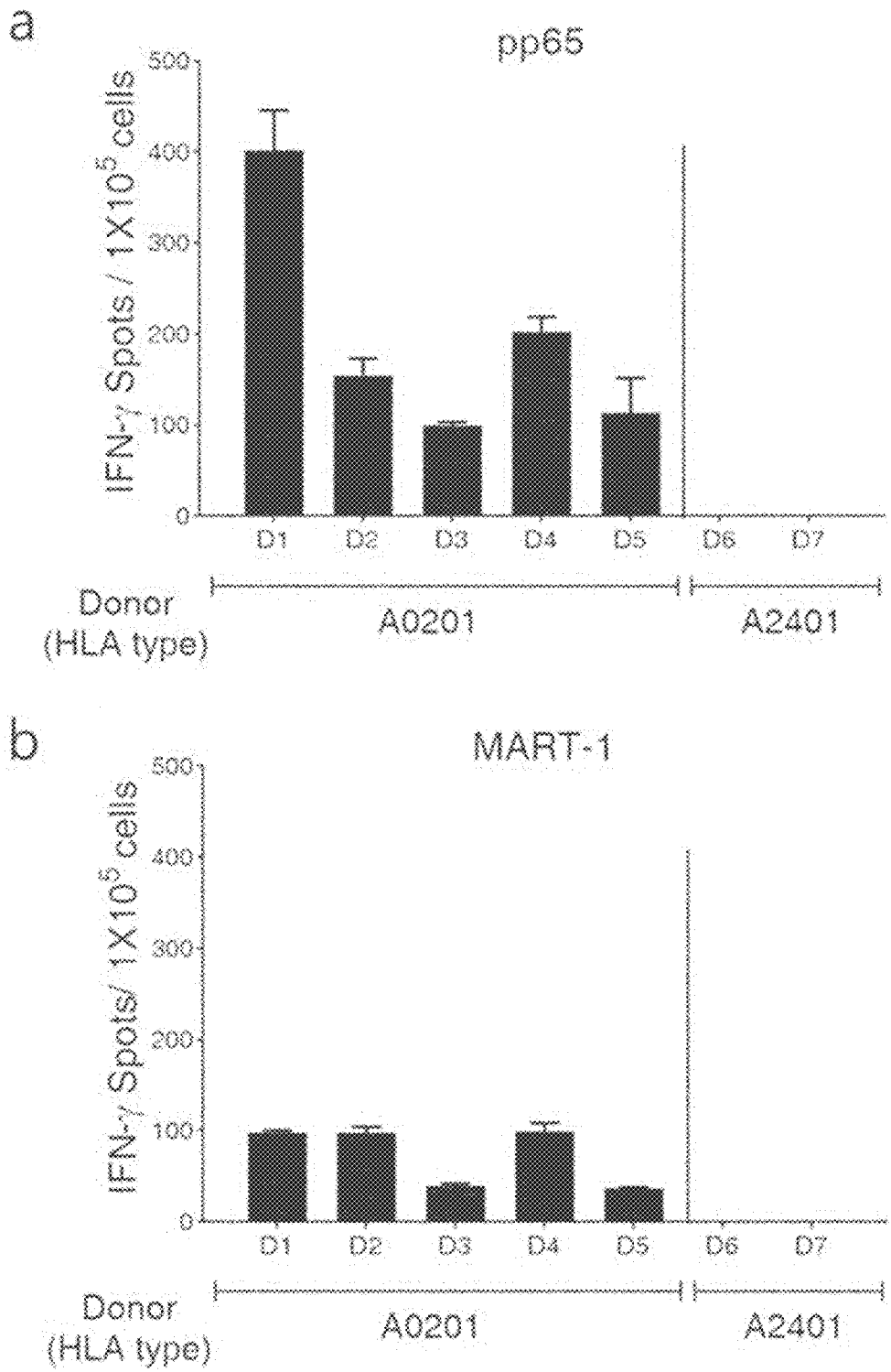
FIG. 7 shows results of evaluating indirect effects of an exosome by examining the transfer of exosome surface molecules to CD8+ T cells or K562 cells.

As illustrated in FIG. 7a, when the four groups were treated with the exosome and the stimulation of IFN-γ-secreting T cells was confirmed, Group 1 exhibited the strongest response because the exosome transferred co-stimulatory molecules and HLA-A2 to CD8+ T cells and also directly stimulated CD8+ T cells, and Group 2 exhibited an intermediate level of immune response because CoEX-A2 was transferred to CD8+ T cells. In Group 3, a direct immune response of CoEX-A2 was confirmed.

In order to confirm the migration of HLA-A2 and co-stimulatory molecules expressed in the exosome, K562 cells and the exosome were co-cultured and washed, and then treated with antigens. Through ELISPOT, this experiment confirmed that the co-stimulatory molecules and HLA expressed in the exosome were transferred to K562, and these K562 cells could stimulate CD8+ T cells (FIG. 7b). As a result, it can be seen that CoEX-A2 may directly stimulate CD8+ T cells or stimulate CD8+ T cells by delivering surface substances to other cells.

<Experimental Example 4> Comparison of CoEX-A2 and DEX in CD8+ T Cell Stimulation Finally, the inductions of viral and tumor antigen-specific CD8+ T cells of CoEX-A2 and DEX were compared.

Figure 8A:
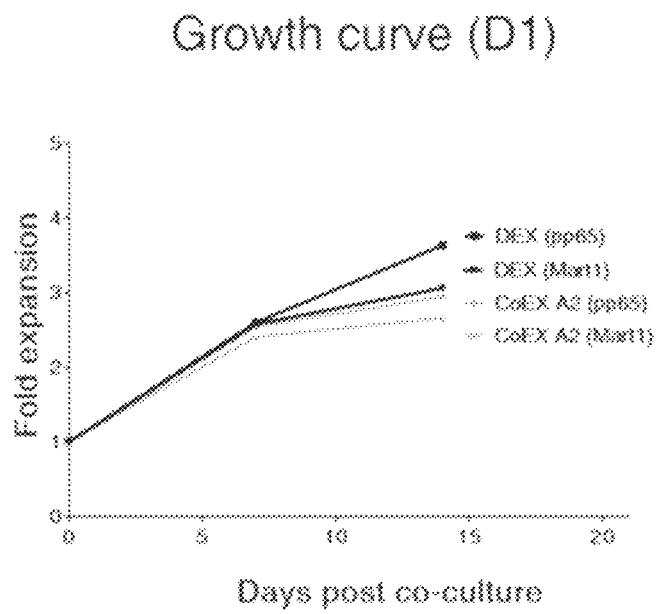
FIG. 8a illustrates the proliferation results of CD8+cells stimulated by an exosome (CoEX-A2) which expresses pp65 or MART1 peptide-pulsed co-stimulatory molecules and HLA-A2 molecules.
Figure 8B:
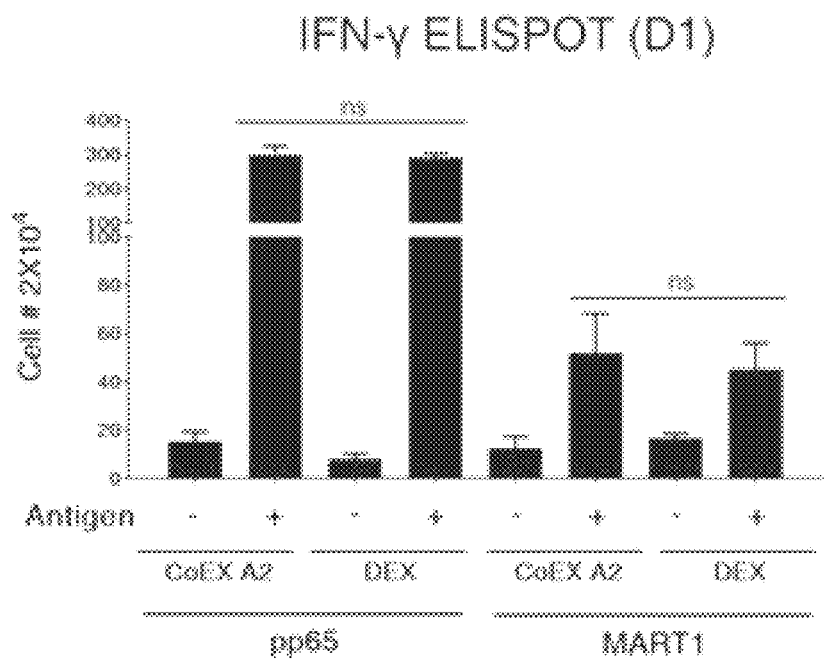
FIG. 8b illustrates the IFN-γ ELISPOT analysis results performed by using pp65 or MART1 peptide-pulsed CoEX-A2 in order to measure the frequency of antigen-specific T cells.
Figure 8C:
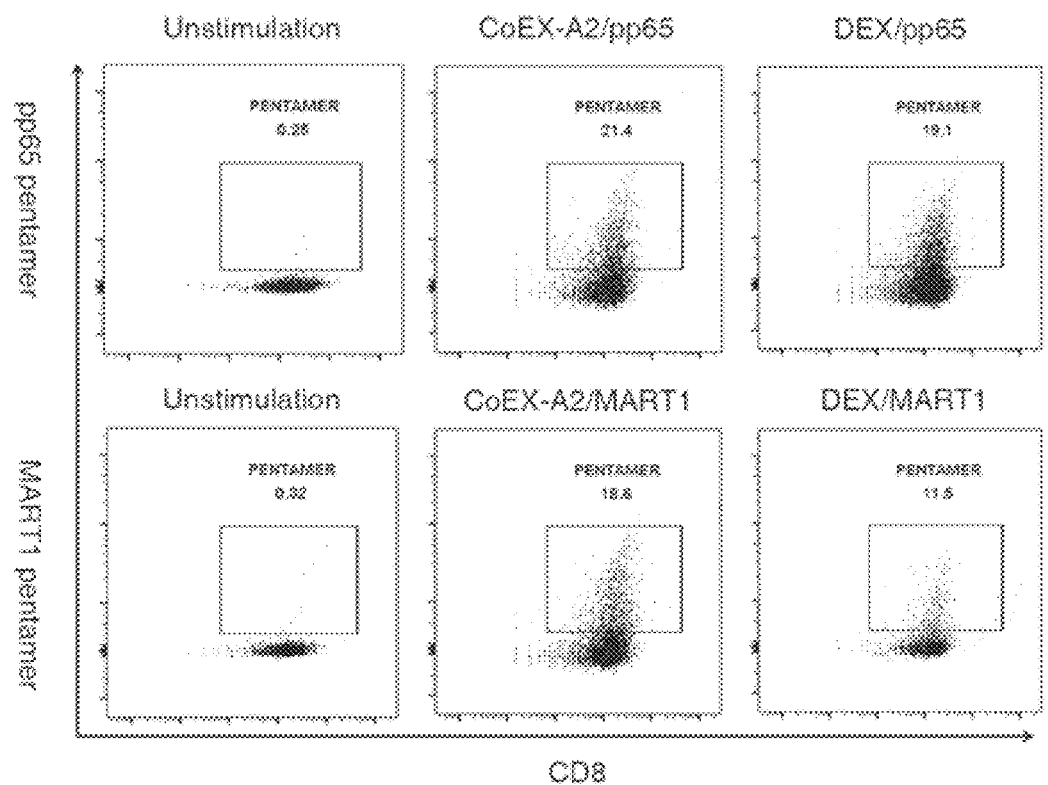
FIG. 8c illustrates the flow cytometry analysis results thereof, and CD8+T cells were stimulated by CD80, CD83, and the 4-1BB ligand (4-1BBL; known as CD137L) for the proliferation of clones. In vitro expansion was achieved by the addition of the modified exosome which expresses feeder cells or co-stimulatory ligands.

As illustrated in FIGS. 8a to 8c, the proliferation level of CD8+ T cells was induced to a level similar to that of DEX when CD8+ T cells were treated with CoEX-A2. Even when cultured for 14 days or more, pp65- and MART1-specific CD8+ T cells were increased to an extent similar to DEX when treated with CoEX-A2.

In order to confirm the cytotoxicity of CD8+ T cells induced by CoEX-A2/pp65 and DEX/pp65, T cells treated with a pp65 peptide were tested as a target. The death rate of target cells was confirmed by staining with 7-AAD (viability dye) (FIG. 9a).

Further, CoEX-A2/pp65 CD8+ T cells and DEX/pp65 CD8+ T cells were tested by setting the ratio of effector: target cells at 6.25:1, 12.5:1, 25:1, 50:1, 100:1, and 200:1.

Figure 9:
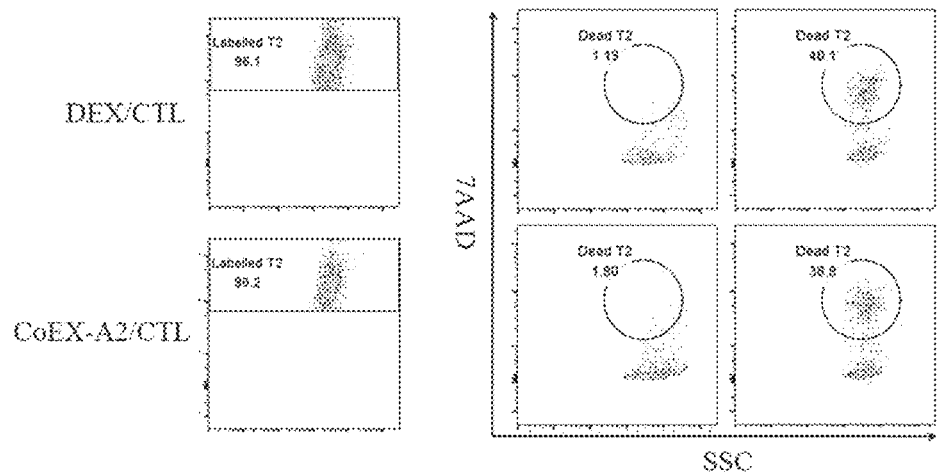
FIG. 9 is a set of results illustrating that exosomes (CoEX-A2/pp65) which express HLA-A2 and co-stimulatory molecules and are loaded with pp65 exhibit CD8+ T cell stimulation at a level similar to that of dendritic cell-derived exosome (DEX)/pp65.
Figure 9:
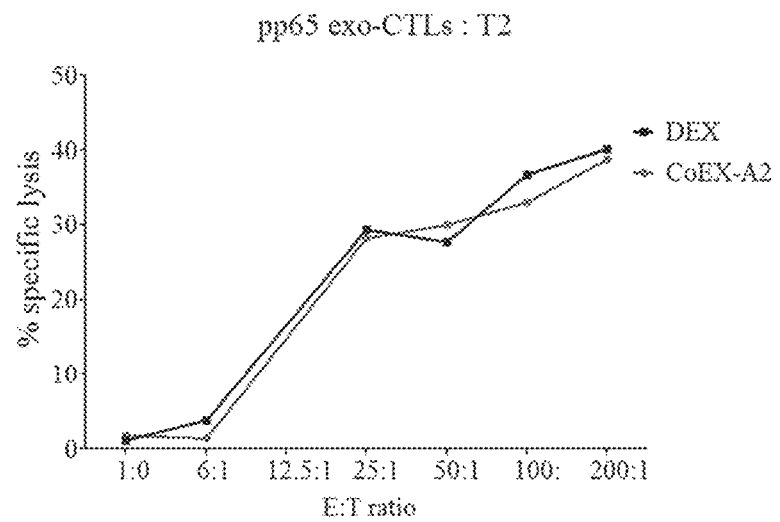

As a result of the experiment, there was no significant difference between CD8+ T cell groups according to the ratio of effector:target cells (FIG. 9b).

From the result, CoEX-A2 could produce antigen-specific CD8+ T cells in vitro, and direct and indirect stimulation abilities of these exosomes were similar to that of DEX.

The present invention may be applied to the field of prevention or treatment of tumors, pathogen infections, or autoimmune diseases.

What is claimed is:

1. A method for proliferating T cells comprising
a step of co-culturing an exosome and any one T cell of a CD4 T cell, a CD8 T cell, or a γδT cell;
wherein the exosome expresses a human leukocyte antigen (HLA), CD32, CD80, CD83, and 4-1BBL.

2. The method of claim 1, wherein the exosome is derived from artificial antigen-presenting cells prepared by introducing nucleic acids encoding HLA, CD32, CD80, CD83, and 4-1BBL into cells which do not express HLA Class I and II molecules.

3. The method of claim 2, wherein the cells which do not express HLA Class I and II molecules are any one of K562 cells and modified 293T cells.

4. A method for proliferating T cells comprising
a step of co-culturing an exosome and any one T cell of a CD4 T cell, a CD8 T cell, or a γδT cell;
wherein the exosome expresses a human leukocyte antigen (HLA); CD32; CD80; CD83; 4-1BBL; and one or more selected from the group consisting of CD40L, CD70, and OX40L.

* * * * *